US006897238B2

(12) United States Patent
Anderson

(10) Patent No.: US 6,897,238 B2
(45) Date of Patent: May 24, 2005

(54) TOPICAL AMINOLEVULINIC ACID-PHOTODYNAMIC THERAPY FOR THE TREATMENT OF ACNE VULGARIS

(75) Inventor: Richard Rox Anderson, Lexington, MA (US)

(73) Assignee: General Hospital Corporation, Boston, MA (US)

( * ) Notice: Subject to any disclaimer, the term of this patent is extended or adjusted under 35 U.S.C. 154(b) by 15 days.

(21) Appl. No.: 09/929,384

(22) Filed: Aug. 14, 2001

(65) Prior Publication Data

US 2002/0099094 A1 Jul. 25, 2002

Related U.S. Application Data

(60) Provisional application No. 60/225,691, filed on Aug. 16, 2000.

(51) Int. Cl.$^7$ .................. A61K 31/195; A61K 7/42
(52) U.S. Cl. ................. 514/563; 514/561; 514/814; 424/59
(58) Field of Search .................. 514/561, 814, 514/563, 410; 424/59, 60

(56) References Cited

U.S. PATENT DOCUMENTS

| | | | |
|---|---|---|---|
| 4,287,554 A | 9/1981 | Wolff | |
| 4,651,739 A | 3/1987 | Oseroff et al. | |
| 4,803,069 A | * 2/1989 | Kekesi et al. .................. | 424/74 |
| 4,930,504 A | 6/1990 | Diamantopoulos et al. | |
| 4,945,908 A | 8/1990 | Schneider | |
| 5,019,034 A | 5/1991 | Weaver et al. | |
| 5,131,403 A | 7/1992 | Hayes | |
| 5,226,907 A | 7/1993 | Tankovich | |
| 5,234,940 A | * 8/1993 | Kennedy et al. ............. | 514/410 |
| 5,304,170 A | 4/1994 | Green | |
| 5,422,093 A | * 6/1995 | Kennedy et al. ........... | 424/9.61 |
| 5,423,803 A | 6/1995 | Tankovich et al. | |
| 5,425,728 A | 6/1995 | Tankovich | |
| 5,445,611 A | 8/1995 | Eppstein et al. | |
| 5,464,436 A | 11/1995 | Smith | |
| 5,520,905 A | * 5/1996 | Uhlmann et al. .............. | 424/59 |
| 5,647,866 A | 7/1997 | Zaias et al. | |
| 5,669,916 A | 9/1997 | Anderson | |
| 5,713,845 A | * 2/1998 | Tankovich ................... | 604/20 |
| 5,733,572 A | 3/1998 | Unger et al. | |
| 5,735,844 A | 4/1998 | Anderson et al. | |
| 5,752,948 A | 5/1998 | Tankovich et al. | |
| 5,752,949 A | 5/1998 | Tankovich et al. | |
| 5,817,089 A | 10/1998 | Tankovich et al. | |
| 5,856,566 A | * 1/1999 | Golub ........................ | 562/567 |
| 5,925,034 A | 7/1999 | Buckley et al. | |
| 5,955,490 A | * 9/1999 | Kennedy et al. ............. | 514/410 |
| 6,036,684 A | 3/2000 | Tankovich et al. | |
| 6,063,108 A | 5/2000 | Salansky et al. | |
| 6,165,170 A | 12/2000 | Wynne et al. | |
| 6,168,590 B1 | 1/2001 | Neev | |
| 6,183,773 B1 | 2/2001 | Anderson | |
| 6,283,956 B1 | 9/2001 | McDaniel | |
| 6,306,130 B1 | 10/2001 | Anderson et al. | |
| 6,385,272 B1 | 5/2002 | Takahashi | |
| 2002/0087205 A1 | * 7/2002 | Chen .......................... | 607/88 |

FOREIGN PATENT DOCUMENTS

| | | |
|---|---|---|
| EP | 0 726 083 A2 | 8/1998 |
| EP | 0 726 083 A3 | 12/1998 |
| WO | WO 94/06424 | 3/1994 |
| WO | WO94/06424 * | 3/1994 |
| WO | WO 95/07077 | 3/1995 |
| WO | WO95/07077 * | 3/1995 |
| WO | WO 96/14899 | 5/1996 |
| WO | WO 96/39188 | 12/1996 |
| WO | WO 96/41579 | 12/1996 |
| WO | WO 97/00098 | 1/1997 |
| WO | WO 98/33444 | 8/1998 |
| WO | WO 98/52610 | 11/1998 |
| WO | WO 98/53847 | 12/1998 |

OTHER PUBLICATIONS

Joris Kloek and Gerard M.J. Beijersbergen van Henegouwen, Photochemistry and Photobiology, Prodrugs of 5–Aminolevulinic Acid for Photodynamic Therapy, pp. 994–1000, 64(6), (1996).

Hongcharu et al., The Society for Investigative Dermatology, Inc., Topical ALA–Photodynamic Therapy for the Treatment of Acne Vulgaris, pp. 1–9 (2000).

Peng et al., Journal of Photochemistry and Photobiology B. Biology 34, Build up of esterfield aminolevulinic–acid–derivative–induced porphyrin fluorescence in normal mouse skin, pp. 95–96 (1996).

Mutzhas, et al. "A New Apparatus with High Radiation Energy Between 320–460 nm: Physical Description and Dermatological Applications" *The Journal of Investigative Dermatology*, vol. 76 pp. 42–47 (1981).

Gfesser, et al., "Seasonal Variations in the Severity of Acne Vulgaris" *International Journal of Dermatology*, vol. 35, No. 2, pp. 116–117 (1996).

Sigurdsson et al "Phototherapy of Acne Vulgaris with Visible Light" *Dermatology*, vol. 194, pp. 256–260 (1997).

(Continued)

*Primary Examiner*—Vickie Kim
(74) *Attorney, Agent, or Firm*—Nutter, McClennen & Fish LLP

(57) ABSTRACT

Light treatments of sebaceous gland disorders with 5-aminolevulinic acid and photodynamic therapy are disclosed. A preferred treatment includes topical application of 5-aminolevulinic acid to the skin followed by light exposures with repeated treatment at various intervals. At low doses of ALA and photodynamic therapy (PDT) in single or multiple treatments, improvement in the sebaceous gland disorder, e.g., acne, provides the discovery that diminishment in sebum secretion and the eradication of bacteria occurs. At high doses of ALA and a single high energy PDT treatment, permanent changes to the sebaceous gland and sebum secretion have been discovered.

13 Claims, 15 Drawing Sheets

OTHER PUBLICATIONS

Arakane et al. "Singlet Oxygen Generation from Coproporphyrin in Propionibacterium acnes on Irradiation" *Biochemical and Biophysical Research Communications*, vol. 223, article 0937, pp. 578–582 (1996).

Kjeldstad et al. "Changes in Polyphosphate Composition and Localization in Propionibacterium Acnes After Near–Ultraviolet Irradiation" *Can J. Microbiol*, vol. 37, pp. 562–567 (1991).

Naess et al. "In Vivo and in Vitro Effects of Doxycycline on Leucocyte Membrane Receptors" *Clin. exp Immunol*, vol. 62, pp. 310–314 (1985).

Kollias, et al. "Endogenous Skin Fluorescence Includeds Bands that may Serve as quantitative Markers of Aging and Photoaging" *The Journal of Investigative Dermatology*, vol. 111, No. 5, pp. 776–780 (1998).

Brookner, et al. "Safety Analysis: Relative Risks of Ultraviolet Exposure from Fluorescence Spectroscopy and Colposcopy Are Comparable" *Photochemistry and Photobiology*, vol. 65, No. 6 pp. 1020–1025 (1997).

Konig, et al. "Photodynamic Induced Inactivation of Propionibacterium Acnes Using the Photosensitizer Methylene Blue and Red Light" *Dermatologische Monatsschrift*, vol. 178, pp. 297–300 (1992).

Dierickx, et al. "Photodynamic Therapy for Nevus Sebaceus with Topical Aminolevulinic Acid" *Arch Dermatol*, vol. 133, pp. 637–640 (1999).

Konig, et al. "photodynamische Akitvitat von methylenblau" *Akt. Dermatol*, vol. 19, pp. 195–198 (1993).

Konig, et al. "Photodynamically Inactivation of Propionibacterium Acnes" *SPIE*, vol. 3247 pp. 106–110 (1998).

Mills, et al. "Ultraviolet Phototherapy and Photochemotherapy of Acne Vulgaris" *Arch Dermatol*, vol. 114, pp. 221–223 (1978).

Wilkin "Pathophysiology and Treatment" *Arch Dermatol*, vol. 130, pp. 359–362 (1994).

Phillips, et al. "Recent Advances in Dermatology" *The New England Journal of Medicine*, vol. 326, No. 3, pp. 167–178 (1992).

* cited by examiner

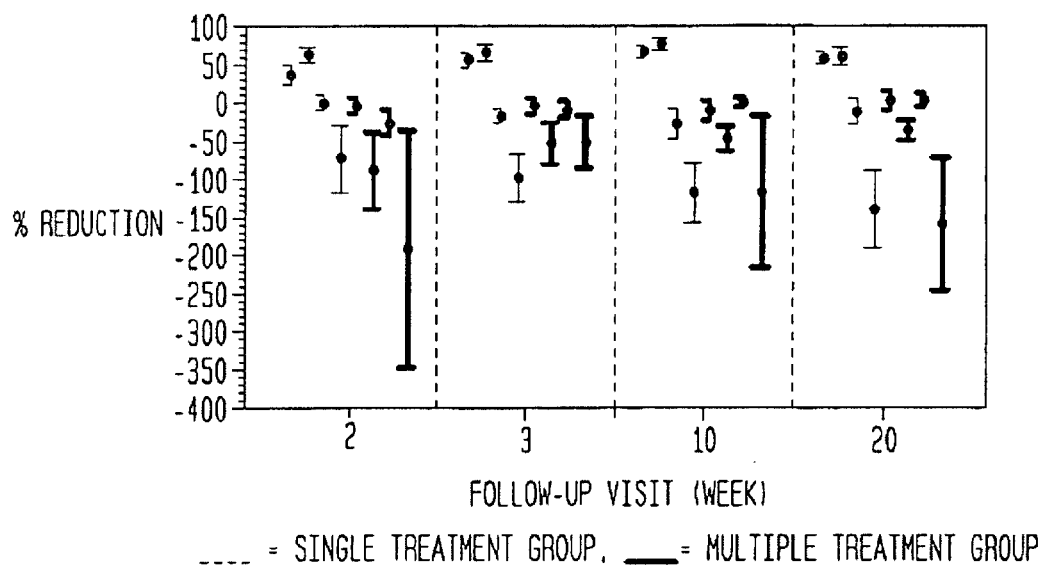
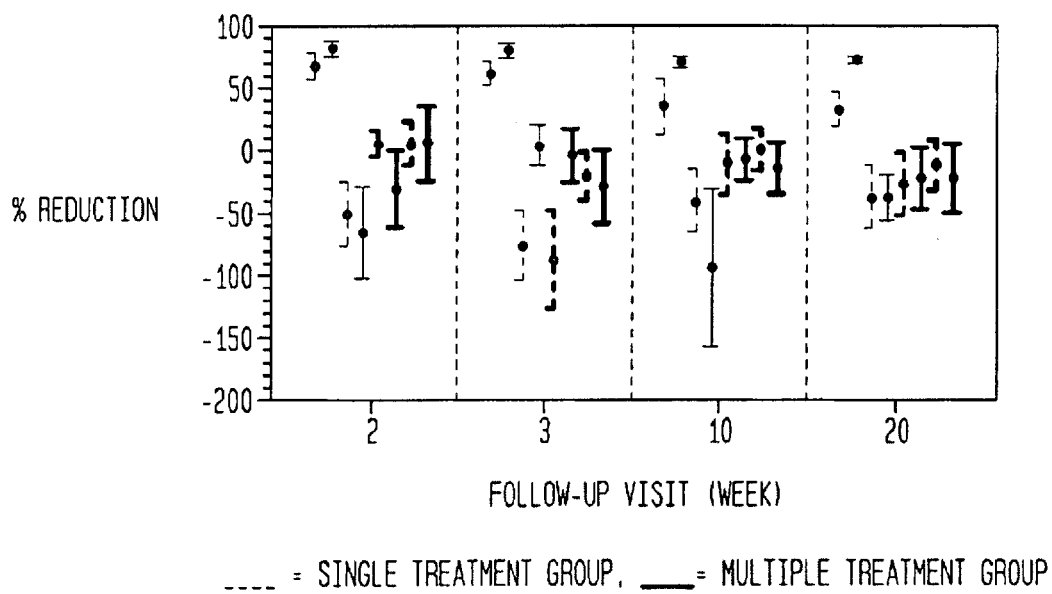

A

B

C

D

A

B

C

D

TOPICAL AMINOLEVULINIC ACID-PHOTODYNAMIC THERAPY FOR THE TREATMENT OF ACNE VULGARIS

CROSS-REFERENCE TO RELATED APPLICATION

This application is related to and claims the priority under 35 USC §119 (e) of U.S. Provisional Application 60/225,691, filed Aug. 16, 2000.

This application is also related to International Application Ser. No. PCT/US01/41691 filed with the same application title on Aug. 13, 2001 in the United States Receiving Office using Express Mail Label No. EL835838321 .

BACKGROUND OF THE INVENTION

Skin disorders, such as acne, can be irritating and embarrassing. The major disease of skin associated with sebaceous follicles, is acne vulgaris. This is also the most common reason for visiting a dermatologist in the United States. There are many treatments, but no cures for acne. These include antibiotics (which inhibit growth of *p. acnes* bacteria which play a role in acne), retinoids such as Accutane® (isotetinoin, which reduces sebaceous gland output of sebum), and antimicrobials such as benzoyl peroxide. Acne lesions result from the rupture of a sebaceous follicle, followed by inflammation and pus (a "whitehead"), or by accumulation of plugged material in the sebaceous follicle (a "blackhead"). This pathophysiology has two major requirements: (1) plugging of the upper portion of the follicle, and (2) an increase in sebum production. The upper portion of the follicle, i.e., the "pore" into which sebum is secreted and which is directly in communication with the skin surface, is called the infundibulum. A plug forms in the infundibulum from cells, sebum, bacteria, and other debris. The sebaceous gland continues to produce sebum (an oily fluid), stretching the infundibulum until either it or some lower portion of the follicles ruptures.

Generally, only a minority of sebaceous hair follicles on the face and upper back develop acne lesions. Therefore, it is likely that some structural differentiation predisposes a fraction of the follicles to develop acne. In most males, acne is worst in the teenage years and then subsides, suggesting that a subpopulation of follicles may be present which ultimately self-destruct. In women, teenage acne is often followed by menstrual acne flares well into adulthood. Since both plugging of the infundibulum and high sebaceous gland activity are necessary for an acne lesion to develop, it is likely that two of the predisposing factors for the follicles which become infected are (1) an infundibulum shape which is easily plugged, and/or (2) a hyperactive sebaceous gland.

Unlike medical dermatology, most laser dermatology treatments are actually "cures"-producing a permanent anatomic, microsurgical effect on the skin. This includes skin resurfacing, portwine stain treatment, tattoo and pigmented lesion removal, and hair removal. Selective photothermolysis or controlled skin ablation with lasers or other extremely intense light sources, might therefore be capable of curing skin disorders, such as acne, if appropriately targeted to the primary site(s) of pathophysiology.

Therefore a need exists which circumvents and provides a solution to the above-described shortcomings of the presently known treatments.

SUMMARY OF THE INVENTION

The present invention is based, at least in part, on the discovery that 5-aminolevulinic acid (ALA) described infra, in combination with an energy source, e.g., photo (light) therapy, can be used to modulate, e.g., treat, sebaceous gland disorders, e.g., eliminate, inhibit, or prevent occurrence or reoccurrence of the skin disorder. Topically-applied ALA is taken up by epithelial cells and metabolized via the porphyrin pathway to protoporphyrin IX (PpIX), the precursor of heme. PpIX is a photosensitizer that accumulates not only in the epidermal cells, but also the pilosebaceous units. When intense light, e.g., visible light, red light, light with a wavelength range of between about 320 and 700 nm, is delivered to the ALA-treated skin, PpIX is excited into a triplet state, which reacts with oxygen to produce singlet oxygen, causing membrane damage and cell destruction. Topical ALA may directly enter hair follicles, where sebaceous glands actively synthesize and retain PpIX.

The present treatment protocol is efficient, is topical, and provides relief of the sebaceous gland disorder for at least 20 weeks. Moreover, the present invention provides optimized conditions for treatment of skin, such that the therapeutic treatment is non-irritating, long lasting (greater than 20 weeks) and can be accomplished in one or more applications. A preferred example of such a sebaceous gland disorder is acne.

The present invention pertains to methods for treating skin disorders associated with sebaceous follicles by topically applying 5-aminolevulinic acid (ALA) to a section of skin afflicted with a sebaceous gland disorder, wherein the ALA is converted into PpIX which is then activated by energy that penetrates outer layers of epidermis. A sufficient amount of the ALA infiltrates the afflicted section of skin, is converted into PpIX, and is exposed to sufficient energy to cause the PpIX to become photodynamically activated, thereby treating the sebaceous gland disorder. In one embodiment, the sebaceous gland disorder is acne. Suitable energy sources for photodynamic treatment include flash lamp based sources and lasers, such as Nd: YAG, Alexandrite, flash lamp-pumped dyes and diodes. Alternatively, the energy source can also be a continuous wave energy source. In preferred embodiments, the ALA is dissolved in an aqueous/alcoholic solution in concentrations between about 10% and 20% by weight.

The present invention also pertains to methods for modifying the opening to the infundibulum by topically applying ALA to the opening to the infundibulum, wherein the ALA is converted into PpIX, that is then photodynamically activated by energy which penetrates outer layers of epidermis. A sufficient amount of the ALA infiltrates spaces about the infundibulum and the infundibulum is exposed to sufficient energy to cause the converted ALA to become photodynamically activated, thereby modifying the opening to the infundibulum. In one embodiment, the opening to the infundibulum is increased. In still another embodiment, the opening to the infundibulum is altered such that pore pluggage will not occur, e.g., the infundibulum is reshaped such that excess sebum, oils, dirt and bacteria will not cause pore pluggage to occur, resulting in a black head (comedon) or white head (milium).

The present invention also pertains to methods for suppressing, e.g., decreasing, the oil/lipid output production of the sebaceous gland. Application of ALA to the pilosebaceous unit, e.g., the sebaceous gland, followed by photodynamic stimulation of the resultant PpIX by an energy source can cause selective permanent physical alteration to the sebaceous gland and/or follicle such that surrounding tissue remains unaffected. The physical alteration to the sebaceous gland and/or follicle results in diminished production of sebum and the size of the sebaceous gland is decreased.

The present invention further pertains to methods for modifying the pilosebaceous unit by topically applying ALA to the pilosebaceous unit, wherein the resultant PpIX is photodynamically activated by energy which penetrates into the dermis and into the outer layers of epidermis. A sufficient amount of ALA infiltrates the pilosebaceous unit and the pilosebaceous unit is exposed to sufficient energy to cause the increased levels of PpIX to become photodynamically activated, thereby modifying the pilosebaceous unit. In one embodiment, the pilosebaceous unit is treated such that sebum production is diminished. A decrease in pore pluggage can occur, as a result of the diminishment of sebum production. In one preferred embodiment, treatment of the pilosebaceous unit by the present invention results in elimination of pore pluggage, e.g., the pilosebaceous unit is treated such that excess sebum, oils, dirt and bacteria will not cause pore pluggage to occur, resulting in a black or white head.

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE INVENTION

Figure 1A:
FIG. 1 shows transient acneiform eruption caused by a single PDT treatment, a) Baseline, b) 1 week post treatment.

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

5-Aminolevulinic acid, also known as 5-aminolaevulinic acid, delta-aminolevulinic acid, delta-aminolaevulinic acid, or 5-amino4-oxopentanoic acid, is an intermediate in the pathway to the production of the photosensitizer, proptoporphyrin IX (PpIX). In the present invention, 5-Aminolevulinic acid can be used as a salt, such as the hydrochloride salt. 5-Aminolevulinic acid can also be used in a pharmacologically equivalent form, such as an amide or ester. Examples of precursors and products of 5-aminolevulinic acid and pharmacologically equivalent forms of 5-aminolevulinic acid that can be used in the present invention are described in J. Kloek et al., Prodrugs of 5-Aminolevulinic Acid for Photodynamic Therapy, Photochemistry and Photobiology, Vol. 64 No. 6, December 1996, pages 994–1000; WO 95/07077; Q. Peng et al., Build-Up of Esterified Aminolevulinic-Acid-Derivative-Induced Porphyrin Fluorescence in Normal Mouse Skin, Journal of Photochemistry and Photobiology B: Biology, Vol. 34, No. 1, June 1996; and WO 94/06424. These references are incorporated herein in their entirety. The term "ALA" refers to all of the above-referenced compounds as described herein.

The present invention is based, at least in part, on the discovery that ALA leads to increased concentration of PpIX in epithelial cells, hair follicles, the pilosebaceous unit, the infundibulum and/or sebaceous glands, and in combination with an energy source, photodynamic therapy can be used to treat sebaceous gland disorders, e.g., eliminate, remove, or prevent occurrence or reoccurrence of the sebaceous gland disorder. Examples of such sebaceous gland disorders include sebaceous gland hyperplasia, acne vulgaris and acne rosacea. A preferred example of such a sebaceous gland disorder is acne.

The term "photodynamic" refers to the administration of a photosensitizing agent to a subject, including administration of a precursor of a photosensitizing agent such as ALA, and subsequent irradiation with energy, e.g., light, of the target cells or tissue of the subject. It is believed that ALA and hence, the photosensitizing agent preferentially accumulate in the target cells, because they are of an infective origin, e.g., bacteria. It has now been surprisingly discovered that the administration of ALA, as a result of their more rapid proliferation, causes the target cells or tissue contain relatively greater concentrations of light sensitive porphyrins, e.g., PpIX, and thus are more sensitive to light. Thus, the targeted tissue (hair follicles, infundibulum, sebaceous gland, pilosebaceous unit) containing sufficiently high concentrations of the photosensitizing agent, including the metabolites of ALA, selectively absorb greater amounts of energy and can be selectively localized and distinguished from the adjacent cells or tissues. Photodynamic activation of the photosensitizing agent destroys the cells/tissue with increased concentrations of the photosensitizing agent. In particularly preferred embodiments, bacteria present in the sebaceous gland are eradicated. The effect of the light is dependent upon the photosensitizer selected wavelength or range of wavelengths, as well as the intensity and duration of administration of the energy, e.g., light.

In one aspect, the present invention is drawn to methods for treating sebaceous gland disorders by topically applying ALA to a section of skin afflicted with a sebaceous gland disorder. The ALA is converted in PpIX via the protoporphyrin pathway, and the resultant photosensitizer PpIX is energetically stimulated by an energy source. A sufficient amount of ALA infiltrates the skin and the section of skin is exposed to at least one frequency band of energy so as to impart, to the converted ALA, sufficient energy to cause the resultant PpIX to become photodynamically activated resulting in a physiological change, thereby treating the sebaceous gland disorder. In one embodiment, the sebaceous gland disorder is acne. Suitable energy sources include a wide range of pulsed or continuous electromagnetic sources including, optical energy emitted by the sun, ultraviolet light generators, flash lamp based sources and lasers, such as Nd:YAG, Alexandrite, and flash lamp-pumped dye lasers and diode lasers. Alternatively, the energy source can be a continuous wave energy source, such as arc lamps, tungsten-halogen lamps and light-emitting diodes.

In preferred embodiments, the energy source emits visible light, especially red visible light. Generally, the range of energy applied to the skin surface ranges from 1 $J/cm^2$ to about 200 $J/cm^2$, preferably from about 25 $J/cm^2$ to about 200 $J/cm^2$, and most preferably about 100 $J/cm^2$.

In general, the wavelength range for therapeutic treatment is from about 320 nm to about 700 nm, preferably from about 550 to about 700 nm, more preferably from about 550 to about 600 nm.

For example, in one embodiment, the skin is treated with a low dose of ALA and low dose of energy to provide relief from acne. This can be considered a therapeutic treatment in which occasional multiple treatments are required to alleviate the sebaceous gland disorder, e.g., acne. The procedure can be repeated daily, monthly, bimonthly, every three months or as required to maintain the diminishment of the sebaceous gland disorder. A suitable treatment includes topical application of about 0.1 to about 10 weight percent of ALA, preferably between about 0.1 to about 5 weight percent, most preferably between about 0.1 to 1 weight percent of ALA followed by a low dosage of energy, e.g., a range of between about 1 $J/cm^2$ and about 20 $J/cm^2$, preferably between about 1 $J/cm^2$ and about 10 $J/cm^2$, and most preferably between about 1 $J/cm^2$ and 5 $J/cm^2$, e.g., 1 $J/cm^2$. This therapeutic treatment is of great interest in that these lower levels of ALA are effect to destroy the bacteria associated with acne; the bacteria is very sensitive to the ALA-photodynamic therapy. This therapy offers the advantage of utilizing low levels of ALA and energy, such that the patient does not feel discomfort and that the skin becomes hyperpigmented. The individual can undergo treatments on a regular basis to prevent or alleviate the sebaceous gland disorder. In general, the energy utilized has a wavelength range of between about 330 nm and about 650 nm to about 700 nm.

In another embodiment, the skin is treated with a high dose of ALA and a high dose of energy to provide a permanent improvement in the sebaceous gland disorder, e.g., acne. This can be viewed as a permanent therapeutic cure for the affliction in that the sebaceous gland is diminished in size and microscarring occurs to and about the sebaceous gland, thereby decreasing or eliminating the secretion of sebum. It is believed that the microscarring from the ALA-PDT therapy fixes the size of the sebaceous gland so that it cannot expand to once again produce large quantities, relatively, of sebum. The microscarring and the reduction of sebaceous gland size and sebum production has been 6 months after a single treatment. A suitable permanent treatment includes topical application of about 10 to about 30 weight percent of ALA, preferably between about 10 and about 20 weight percent ALA, and most preferably about 20 weight percent ALA followed by a high dose of energy, e.g., a range of between about 50 $J/cm^2$ and about 200 $J/cm^2$, preferably between about 100 $J/cm^2$ and about 150 $J/cm^2$, and most preferably between about 125 $J/cm^2$ and 175 $J/cm^2$. In this embodiment, the optimal wavelength range is between about 550 nm and about 650 nm.

Typically, ALA is administered topically as a solution. The concentration of the ALA can be in the range from about 0.1 to about 30 percent by weight, preferably from about 0.1 to about 20 percent by weight, and most preferably from about 10 to about 20 percent by weight. The ALA can be formulated into various creams and emulsions that can penetrate into the skin. A preferred solution is a combination of alcohol, ethyl alcohol and water. Generally, ALA is applied topically in an appropriate carrier and permitted to permeate into the skin over a period of about 1 to about 12 hours, preferably from about 2 to about 5 hours, and most preferably about 3 hours. As a general practice, the treated area is covered with material, such as a plastic, which helps to slow evaporation of the solvent of the carrier system. The individual is then subjected to photodynamic therapy to treat the sebaceous gland disorder. In one embodiment, the individual is treated with a 20% ALA in a hydroalcoholic vehicle (Levulan, provided by DUSA Pharmaceuticals) for 3 hours under occlusion with plastic film and 150 $J/cm^2$ of broad band light (550–700 nm).

The present invention also pertains to methods for modifying the opening to the infundibulum by topically applying ALA to the opening to the infundibulum, wherein the ALA is converted into PpIX, and is treated with at least one frequency band of energy which penetrates outer layers of epidermis. A sufficient amount of ALA infiltrates spaces about the infundibulum and the section of skin is exposed to at least one frequency band of energy so as to impart to the converted ALA, PpIX, sufficient energy to cause the PpIX to become photodynamically activated, thereby modifying the opening to the infundibulum. In one embodiment, the opening to the infundibulum is altered such that pore pluggage will not occur, e.g., the infundibulum is reshaped such that excess sebum, oils, dirt and bacteria will not cause pore pluggage to occur, resulting in a blackhead (comedon) or white head (milium). In a preferred embodiment, the opening to the infundibulum is opened.

The present invention further pertains to methods for modifying the pilosebaceous unit by topically applying ALA to the pilosebaceous unit, wherein the resultant PpIX absorbs at least one frequency band of energy which penetrates outer layers of epidermis. A sufficient amount of the ALA infiltrates the pilosebaceous unit and the section of skin is exposed to at least one frequency band of energy so as to impart to the resulting increased concentration of PpIX, sufficient energy to cause the PpIX to become photodynamically activated, thereby modifying the pilosebaceous unit. In one embodiment, the pilosebaceous unit is treated such that sebum production is diminished, thereby resulting in decreased pore pluggage. In one preferred embodiment, treatment of the pilosebaceous unit by the present invention results in elimination of pore pluggage, e.g., the pilosebaceous unit is treated such that excess sebum, oils, dirt and bacteria will not cause pore pluggage to occur, resulting in a black or white head.

In another aspect, the invention includes the combination of ALA with UVA and/or UVB absorbing substances. The combination can be applied topically and is useful in the treatment of sebaceous gland disorders, such as acne. Application of the ALA with the UVA and/or UVB absorbing substance followed by PDT causes the converted ALA to eradicate bacteria associated with acne. Generally, sunlight is the energy source for PDT stimulation and the total fluence of energy is between about 1 and about 100 $J/cm^2$, preferably between about 1 and about 50 $J/cm^2$ and most preferably between about 10 and about 40 $J/cm^2$. Typically the ALA concentration is in the range of between about 0.1 to about 10 percent by weight, preferably between about 0.1 and about 5 percent by weight and most preferably between about 0.1 and 1 percent by weight. In general the UVA and/or UVB filter substances are included in the composition in a range of between about 0.1 to about 30% by weight, preferably from about 0.1 to about 10% by weight and most preferably from about 0.1 to about 5% by weight.

Suitable UVB filters include those which absorb energy between about 290 nm and 320 nm, the so-called UVB range, and are generally derivatives of 3-benzylidene camphor, 4-aminobenzoic acid, cinnamic acid, salicylic acid, benzophenone and 2-phenylbenzimidazole. Examples of oil soluble UVB filters include 3-benzylidene camphor derivatives, e.g., 3-(4-methylbenzylidene)camphor, 3-benzylidene-camphor; 4-aminobenzoic acid derivatives, e.g., 4-(dimethylamino)-benzoic-acid (2-ethylhexyl)ester, 4-(dimethylamino)benzoic-acid-amylester; esters of cinnamic acid, e.g., 4-methoxycinnamic-acid-(2-ethylhexyl) ester, 4-methoxycinnamic-acid-isopentylester; esters of salicylic acids, e.g., salicylic acid(2-ethylhexyl)ester, salicylic acid(4-isopropylbenzyl)ester, salicylic acid-homomenthylester; derivatives of benzophenone, e.g., 2-hydroxy4-methoxybenzophenone, 2-hydroxy-4-methoxy-4'-methylbenzophenone, 2,2'-dihydroxy-4-methoxybenzophenone; esters of benzalmalonic acids, e.g., 4-methoxybenzalmalonic-acid-di(2-ethylhexyl)ester; 2,4,6-trianilino-(p-carbo-2'-ethyl-1'-hexyloxy)-1,3,5-triazin. Examples of water-soluble UVB filter substances include salts of 2-phenylbenzimidazol-5-sulphonic acid including the sodium, potassium or triethanolammonium salt and sulphonic acid; sulphonic acid derivatives of benzophenones, e.g., 2-hydroxy-4-methoxybenzophenon-5-sulphonic acid and its salts; sulphonic acid derivatives of 3-benzylidene camphor such as 4-(2-oxo-3-bornylidene methyl)benzolsulphonic acid, 2-methyl-5-(2-oxo-3-bornylidenemethyl)sulphonic acid and its salts.

UVA substances filter radiation in the range between 320 nm and about. 400 nm, the co-alled UVA range. Derivatives of dibenzoylmethane are predominantly used to protect against rays in the UVA range and include, for example, 1-(4'-tert.butylphenyl)-3-(4'-methoxyphenyl)propane-1,3-dione and 1-phenyl-3-(4'-iso-propylphenyl)propane-1,3-dione.

Sebaceous glands are components of the pilosebaceous unit. They are located throughout the body, especially on the face and upper trunk, and produce sebum, a lipid-rich secretion that coats the hair and the epidermal surface. Sebaceous glands are involved in the pathogenesis of several diseases, the most frequent one being acne vulgaris. Acne is a multifactorial disease characterized by the occlusion of follicles by plugs made out of abnormally shed keratinocytes of the infundibulum (upper portion of the hair follicle) in the setting of excess sebum production by hyperactive sebaceous glands. Various treatment modalities for acne exist that aim in modifying the rate of sebum secretion by the sebaceous glands (e.g., retinoids), inhibiting the bacterial overgrowth in the follicular duct (antibiotics), or decreasing the inflammation of acne lesions (anti-inflammatory agents). Most of these agents are not curative of acne and simply control the disease by affecting one of the aforementioned pathogenic factors. Oral retinoids are a notable exception: they are potent drugs that can achieve a significant cure rate for acne, but their side effect profile often limits their use. Advantages of the present invention include that treatment can permanently alter the pilosebaceous unit, rendering it no longer susceptible to pore pluggage without the side effects associated with oral retinoids.

The term "sebaceous gland disorders" is intended to include those sebaceous gland disorders which can be treated by a photosensitized material, such as PpIX that is converted from ALA. The PpIX can be photodynamically activated, e.g., reactive, such that it is susceptible to photo-activation or stimulation, e.g., light, i.e., laser stimulation. The activation or excitation of the material generates reactive species, such as a triplet state, which can interact with oxygen to produce singlet oxygen, causing membrane damage and cell destruction. The singlet oxygen can interact with the site of pore pluggage, inflammation, bacteria, viruses, etc. and promote, for example, oxidation of those agents which are associated with the disorder. Examples of sebaceous gland disorders which can be treated by the methods of the invention include sebaceous gland hyperplasia, acne vulgaris and acne rosacea. Of particular importance is treatment of acne by the method of the invention.

The term "pluggage" is intended to obstruction of the pores by the buildup of sebum, dirt, bacteria, mites, oils, and/or cosmetics in the pore, e.g., about the infundibulum.

The term "acne" is art recognized and is intended to include acne vulgaris and acne rosacea. Acne vulgaris the most common skin disease seen in dermatologic practice which affects approximately 17 million people in the United States. Its precise cause is unknown, although abnormal keratin production with obstruction of the follicular opening, increased production of sebum (lipids secreted by the androgen-sensitive sebaceous glands), proliferation of *Propionibacterium acnes* (anaerobic follicular diphtheroids), follicular rupture and follicular mites (demodex) are commonly associated with acne.

Skin conditions such as acne are believed to be caused or exacerbated by excessive sebum flow produced by sebaceous glands most of which are adjacent to and discharge sebum into, hair follicles. Sebum is composed of keratin, fat, wax and cellular debris. Sebum forms a moist, oily, acidic film that is mildly antibacterial and antifungal and may to some extent protect the skin against drying. It is known that the bacteria which contribute to acne, *Propionibacterium acnes* or (P-acnes), grows in sebum. Significant sebum flow in humans begins at puberty. This is when acne problems generally arise. The methods of the present invention decrease or eliminate the overproduction of sebum and thereby eliminates acne.

Not to be limited by theory, photodynamic stimulation of a photosensitizing agent, e.g., PpIX, can cause oxidation and decomposition of the unwanted material(s), thereby degrading and removing unwanted material from the pore. Additionally, this treatment can also cause the opening to the infundibulum to become modified, e.g., the pore opening is enlarged. Consequently, alteration of the pore opening, such as enlargement of the pore opening, a change in the pore shape, or enlargement of the pore opening prevents unwanted dirt, bacteria, viruses and/or oils from building up in the treated area, e.g., the infundibulum.

Preferably, the energy source produces an exposure area of between about 3 to about 100 millimeters to treat a section of skin afflicted with a sebaceous gland disorder, as described above. The fluence is limited such that the skin is not damaged while the sebaceous gland disorder is treated, e.g., eradicated, inhibited, or prevented. The fluence is controlled such that localized destruction to the undesired sebaceous gland disorder occurs with little or no non-specific necrosis of surrounding tissue.

Suitable energy sources include light-emitting diodes, incandescent lamps, xenon arc lamps, lasers or sunlight. Suitable examples of continuous wave apparati include, for example, diodes. Suitable flash lamps include, for example pulse dye lasers and Alexandrite lasers. Representative lasers having wavelengths strongly absorbed by PpIX, within the epidermis and infundibulum, or sebaceous gland, include the short-pulsed green dye laser (504 and 510 nm), yellow long-pulsed dye laser (585–600 nm)the copper vapor laser (511 nm) and the Q-switched neodymium (Nd):YAG laser having a frequency doubled wavelength using a potassium diphosphate crystal to produce visible green light having a wavelength of 532 nm. Further examples of lasers which are suitable for use as energy sources include those in the following table of lasers:
Types of Laser
Commercial Laser Types, Organized by Wavelength

| Wavelength, mm | Type | Output type and power |
|---|---|---|
| 0.532 | Doubled Nd-YAG | Pulsed to 50 W or CW to watts, pulsed or CW for 50 W average power |
| 0.578 | Copper vapor | Pulsed, tens of watts |
| 400–700 nm | Pulsed Dye | 0.1 to 10 Joules |
| 514.5 nm | Ar Ion | up to tens of watts |
| 530.9 nm | Kr Ion | approximately 5 watts |
| 600–900 nm | GaAlAs semiconductor diode array | tens of watts depending on design |

The depth of penetration of the energy, e.g., light, emitted from the energy source, such as a laser, is dependent upon its wavelength. Wavelengths in the visible in to near IR have the best penetration and are therefore best for use to treat the sebaceous gland and infundibulum located within the dermis.

For example, ALA, adapted to accumulate selectively in the infundibulum and/or the sebaceous gland, is first applied to the region of afflicted skin to be treated. Following absorption of the ALA, the ALA undergoes conversion to PpIX via the porphyrin synthetic pathway, is exposed to an energy source, e.g., a laser, capable of producing a wavelength readily absorbed by the converted ALA, e.g., PpIX, thereby selectively photodynamically treating those regions of the dermis known to have trapped oils, bacteria, dirt, etc.

i.e., the pilosebaceous unit, which includes the pore opening, infundibulum and sebaceous gland. Because the PpIX is selectively concentrated within or about these undesired deposits, the deposits are degraded by photodynamically reactive species generated from the activated material. There is minimal to no destruction of normal adjacent epidermal and dermal structures.

Preferably, the treatment of the invention modifies the pore opening to the infundibulum such that the geometry, e.g., the shape, of the opening is permanently altered. Adjustment of the concentration of the ALA and the amount of energy applied by the energy source effects the increased opening size of the pore, thereby preventing accumulation of dirt, oils, and/or bacteria, in that follicle. The operator will need to assess the parameters to illicit the desired effect and will be determined on a patient by patient basis. Generally, it is most desirable to alter the shape of the pore, leaving the pore enlarged and no longer prone to buildup of sebum and/or foreign materials which would cause pore pluggage.

As previously stated, the present invention involves the use of energy sources, e.g., lasers, to target sebaceous glands and cause their photodynamic alteration, e.g., diminishment in size. Sebaceous glands are mainly composed of amorphous lipid material and do not contain effective amounts of PpIX to cause photodynamic stimulation of the tissue/gland/pathogenic species. In order to achieve selective photodynamic treatment of sebaceous glands and confine the extent of any injury in the surrounding tissue, topically applied ALA with selective distribution to the pilosebaceous unit can be utilized. The introduction of ALA in sebaceous glands followed by exposure to energy (light) with a wavelength that corresponds to the absorption peak of the PpIX, will increase the local absorption of light in tissue and lead to selective photodynamic damage of sebaceous glands.

The infundibulum is a critical site in the pathogenesis of many of the disease states, especially acne. There is evidence that abnormal proliferation and desquamation of infundibular keratinocytes leads to the formation of microcomedones and, later on, to clinically visible follicular "plugs" or comedones. Clinically, it appears that some sebaceous follicles are more prone than others to develop acne lesions, possibly due to an inherent structural difference or functional abnormality of the infundibulum, that predisposes them to form plugs and occlude. The self-resolving nature of acne in most patients may reflect the elimination of such "acne-prone" follicles which are eventually replaced by normal skin or fibrosis after repeated bouts of inflammation. If the architecture of the infundibulum is important in the pathogenesis of acne, then selective destruction of this portion of the follicle through ALA assisted energy, e.g., laser, targeting can help eliminate or correct the "pathologic" site by reshaping the infundibulum so as to extrude any occluded material.

Delivery of ALA to the follicle matrix can be achieved by topical application, injection, liposome encapsulation technology, massage, iontophoresis or ultrasonic technology, or other means for delivery of compounds into the dermal region of the skin, e.g., pharmaceutically acceptable carriers.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting ALA of the present invention within or to the subject such that it can performs its intended function. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Preferred carriers include those which are capable of entering a pore by surface action and solvent transport such that the ALA is carried into or about the pore, e.g., into the sebaceous gland, to the plug, into the infundibulum and/or into the sebaceous gland and infundibulum.

Wening agents, emulsifiers and lubricants, such as sodium lauryl sulfate and magnesium stearate, as well as coloring agents, release agents, coating agents, sweetening and perfuming agents, preservatives and antioxidants can also be present in the compositions.

Liquid dosage forms for topical administration of the compounds of the invention include pharmaceutically acceptable emulsions, microemulsions, solutions, creams, lotions, ointments, suspensions and syrups. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, peach, almond and sesame oils), glycerol, tetrahydrofuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

The term "cream" is art recognized and is intended to include semi-solid emulsion systems which contain both an oil and water. Oil in water creams are water miscible and are well absorbed into the skin, Aqueous Cream BP. Water in oil (oily) creams are immiscible with water and, therefore, more difficult to remove from the skin. These creams are emollients, lubricate and moisturize, e.g., Oily Cream BP. Both systems require the addition of either a natural or a synthetic surfactant or emulsifier.

The term "ointment" is art recognized and is intended to include those systems which have oil or grease as their continuous phase. Ointments are semi-solid anhydrous substances and are occlusive, emollient and protective. Ointments restrict transepidermal water loss and are therefore hydrating and moisturizing. Ointments can be divided into two main groups-fatty, e.g., White soft paraffin (petrolatum, Vaseline), and water soluble, e.g., Macrogol (polyethylene glycol) Ointment BP.

The term "lotion" is art recognized and is intended to include those solutions typically used in dermatological applications.

The term "gel" is art recognized and is intended to include semi-solid permutations gelled with high molecular weight polymers, e.g., carboxypolymethylene (Carbomer BP) or methylcellulose, and can be regarded as semi-plastic aqueous lotions. They are typically non-greasy, water miscible, easy to apply and wash off, and are especially suitable for treating hairy parts of the body.

In a one embodiment, liposomes are used to deliver ALA to the follicle matrix. Liposomes provide site-specific transdermal delivery to the follicle matrix. In this embodiment, the ALA is microencapsulated within the liposome and topically applied to the epidermis of the skin.

As noted above, the carrier according to the present invention potentially involves encapsulating the effective amount of ALA within a specific liposome to provide for efficient transdermal delivery of ALA through the layers of the skin. These liposomal compositions are topically applied to the skin and deliver the encapsulated ALA to the follicle region including the sebaceous gland and infundibulum. Following delivery of ALA, irradiation results in highly specific targeting of the follicle matrix and destruction of oils, dirt, bacteria, mites, or viruses within the infected area.

Liposomes are microscopic spherical membrane-enclosed vesicles or sacks (0.5–500 mm in diameter) made artificially in the laboratory using a variety of methods. Within the scope of the present invention, the liposomes should be non-toxic to living cells and they should deliver the contents, in this case ALA, into the follicle and immediately surrounding tissue. The liposomes according to the present invention may be of various sizes and may comprise either one or several membrane layers separating the internal and external compartments.

The liposomes may be made from natural and synthetic phospholipids, and glycolipids and other lipids and lipid congeners; cholesterol, cholesterol derivatives and other cholesterol congeners; charged species which impart a net charge to the membrane; reactive species which can react after liposome formation to link additional molecules to the lysome membrane; and other lipid soluble compounds which have chemical or biological activities.

A general discussion of the liposomes and liposome technology can be found in an article entitled, "Liposomes" by Marc J. Ostro, published in *SCIENTIFIC AMERICAN*, January 1987, Vol. 256, pp. 102–111 and in a three volume work entitled, "Liposome Technology" edited by G. Gregorriadis, 1984, published by CRC press, Boca Raton, Fla. the pertinent portions of which are incorporated herein by reference.

Topically-applied ALA initially enters the infundibulum and later is distributed to the sebaceous glands. It is possible to actively drive the ALA into the follicles by massage, pressure, ultrasound, or iontophoresis, after topically applying the ALA to the skin surface. ALA can be rapidly driven into sebaceous follicles and eccrine sweat ducts by iontophoresis. Wiping the surface with or without a solvent after delivery into the follicles, can be used to remove residual material from the skin surface. Thus, after appropriate application and wiping, the ALA can be preferentially located in follicles, within the infundibula or the infundibula and sebaceous glands.

For photodynamic effects, lower average irradiance exposures given over longer exposure time would be appropriate for example approximately 10–100 mW/cm2 delivered for about 100–2000 seconds (total fluence, 1–200 J/cm2). For photodynamic effect, light sources such as light-emitting diodes, incandescent lamps, xenon arc lamps, lasers or sunlight can be used.

In order to form and retain a plug within the infundibulum, there must be a constriction along the outflow tract. As material including sebum, cells, or bacteria accumulate and are concentrated onto the plug, walls of the infundibulum are dilated until the middle or lower part of the infundibulum is larger in diameter than its outlet (the surface pore). If the outlet diameter can be increased, the plug is more likely to be expelled and pressure within the sebaceous follicle decreased before rupture can occur. The upper region of the infundibulum is also the source of follicular neck cells which shed into the infundibulum and add to the plug. For these reasons, the walls of the upper portion of the infundibulum and especially its pore at the skin surface are the primary target for ALA-assisted sebaceous gland disorder treatment, e.g. acne treatment. In a manner conceptually similar to laser skin "resurfacing", the shape and size of the infundibulum and its outlet pore can be affected by ALA-assisted photodynamic treatment. The dermis immediately surrounding sebaceous follicles, is largely responsible for maintaining shape of the infundibulum, and should be altered to produce a permanent affect.

The invention is further illustrated by the following examples which in no way should be construed as being further limiting. The contents of all references, pending patent applications and published patent applications, cited throughout this application, including those referenced in the background section, are hereby incorporated by reference. It should be understood that the models used throughout the examples are accepted models predictive of efficacy in humans.

EXAMPLES

Photodynamic therapy with topical ALA was tested for the treatment of acne vulgaris, in an open-label prospective human study. Each of 22 subjects with acne on the back was treated in 4 sites with ALA plus red light (ALA-PDT), ALA alone, light alone, and untreated control. Half of the subjects were treated once; half were treated 4 times, 20% topical ALA was applied with 3 hr occlusion, and 150J/cm$^2$ broad band light (550–700 mm) was given. Sebum excretion rate and auto-fluorescence from follicular bacteria were measured before, and at 2, 3, 10, and 20 weeks after treatment. Histologic changes and PpIX synthesis in pilosebaceous units were observed from skin biopsies. ALA-PDT caused a transient acne-like folliculitis. Sebum excretion was eliminated for several weeks, and decreased for 20 weeks after PDT; multiple treatments caused greater suppression of sebum. Bacterial porphyrin fluorescence was also suppressed by PDT. On histology, sebaceous glands showed acute damage and were smaller 20 weeks after PDT. There was clinical and statistically significant clearance of inflammatory acne by ALA-PDT, for at least 20 weeks after multiple ALA-PDT treatments and 10 weeks after a single treatment. Transient hyperpigmentation, superficial exfoliation and crusting were observed, which cleared without scarring. The present methods of the invention provide topical ALA-PDT as an effective treatment of acne vulgaris. ALA-PDT causes phototoxicity to sebaceous follicles, prolonged suppression of sebaceous gland function, and apparent decrease in follicular bacteria after PDT.

Material and Methods
Subject Selection

Twenty-two subjects of both sexes with mild to moderate acne vulgaris (grade 1–4) (Burke et al., 1984) on their backs were enrolled between October 1998 and March 1999. People were excluded if they had used any topical acne treatment, systemic antibiotics in the past 2 weeks, or systemic retinoids in the past 1 year. People were also excluded using medication that could exacerbate or alleviate acne, planning to have excessive sunlight exposure, with a history of keloid or photosensitivity disorder, with Fitzpatrick's skin phototype V–VI, and pregnant or lactating women.

Study design

Subjects were randomly divided into single treatment and multiple treatment groups. Each patient's back was equally divided into four 7.5×10 cm areas for ALA plus red light (ALS-PDT), ALA alone, light alone, and untreated control. Sites were marked withtemplates to precisely relocate each test area. At baseline, clinical evaluations, natural bacterial porphyrin fluorescence photography, and sebum excretion rate (SER) evaluation were performed. Before application of ALA, the skin was cleaned with 70% isopropyl alcohol. Then, 20% topical ALA in a hydroalcoholic vehicle (Levulan, a gift from DUSA pharmaceutical) was applied for 3h under occlusion with plastic film (Saran wrap), and 150 J/cm$^2$ broad band light (550–700 nm) was given to the ALA-PDT and light alone areas. In the multiple treatment group, subjects were treated once a week for 4 consecutive weeks. In this group, if severe exfoliation, erosions or purpura occurred, treatment was postponed to the following week. In both groups, subjects returned one week after treatments for clinical evaluations and at weeks 2, 3, 10 and 20 for clinical, fluorescence, and SER evaluations.

Clinical Evaluations

Each subject's acne was visually assessed using an inflammatory acne score modified from that previously described (Michaelsson et al., 1977). The modification used in this study accounted for both number and size of acne lesions. The numbers of comedo, inflammatory comedo, papules, pustules, nodules and cysts in each test area were recorded. Each type of lesion was given a severity index as follows: 0.5 for comedo (<1 mm), 0.75 for inflammatory comedo, 1 for papule (1 mm–5 mm), 2 for pustule, 3 for nodule (>5 mm), and 4 for inflammatory cyst.

Clinical improvement was globally assessed by 3 dermatologists unaware of the status of treatment, who blindly graded changes in acne from fixed-magnification clinical photographs, after being shown a small set standardized series of training slides not used in the data evaluation. The grading scale was defined as −3 for >50% exacerbation, −2 for 25$^+$–50% exacerbation, −1 for 1$^+$–25% exacerbation, 0 if unchanged, 1 for 1$^+$–25% improvement, 2 for 25$^+$–50% improvement, 3 for 50$^+$–75% improvement, 4 for 75$^+$–99% improvement, and 5 for 100% improvement, as compared to the baseline.

Fluorescence Photography

A Nikon E2N digital camera body with a Nikon 105 mm macro lens was used. A filter (Corion LL-550S) was placed on the lens to block light below 550 nm. The excitation light source was composed of two synchronized photoflashes with Norman 400 watt-second lampheads (FT400/FT6), mounted on a stationary tower with angles of incidence of 60 degrees bilaterally. Two 400 nm bandpass filters with 5 nm bandwidth (Corion S40–400S) were placed on the flashes. By this method, the punctate orange-red fluorescence of hair follicles populated with *P. acnes* was seen. Fluorescence emission has been attributed to bacterial coproporphyrin III and protoporphyrin IX, and intensity of fluorescence is related to the *P. acnes* population. Fluorescence photography was performed at week, 0, 2, 3, 10 and 20 in all sites. The number of punctate red flourescent dots was counted blindly for each test area.

Sebum Excretion Rate (SER) Measurement

Sebum-absorbent tape (Sebutapes, CuDerm Corp, Dallas, Tex.) is a non-invasive, easy and reproducible method to evaluate human sebum output. The subject's skins was shaved, then cleansed for 15 seconds with a cotton gauze soaked in 70% ethanol. When the skin was completely dry, a strip of Sebutape was adhered to each test site for an hour. After removal from the skin, the white tape was placed on a black card for image analysis. Small transparent spots due to sebum excretion from follicles were visualized as a black spot on the white background. A CCD camera and digital frame grabber were used to capture images of the sebutape, then examined using a computer-assisted image analysis (IP-LAB) system. The percentage of sebutape area covered by sebum spots (black) was calculated. Sebutape assays of SER were done this way, at weeks, 0, 2, 3, 10, and 20 in all sites.

Adverse Effects

Adverse effects were scored by clinical evaluation of erythema, edema, loss of epidermis, hyperpigmentation, hemorrhage, vesiculation, and exfoliation on a visual-analogue scale from 0 to 3 (0=absent, 1=mild, 2=moderate, 3=severe) for each finding. Subjective sensation of pain, burning, and itching was generally maximum about 10 minutes into light exposure, and was ranked at that time and the end of treatment (1 hour), by subjects on a scale from 0 to 3 similar to above.

Histologic Examination

Punch biopsy specimens (4 mm) were taken immediately after PDT, a few weeks after PDT, and at 20 weeks from both the untreated control and ALA-PDT areas. Specimens were sectioned in either vertical or horizontal fashion and stained with hematoxylin and eosin, Fontana-Masson, and Masson-Trichrome stains. Histologic examination was performed. Cross-sectioned areas of sebaceous glands, representative sebocytes, and the sebocyte nuclear area were measured from planimetric analysis of serial sectioned specimens of the skin using a computer-assisted planimetry system. Area of sebaceous gland and the cytoplasm/nuclear area ratio in sebocyte were calculated and compared between control and PDT areas at each follow-up. To determine the level of PpIX converted from ALA in the pilosebaceous units, punch biopsy specimens were also taken from ALA-treated areas after 3 h occlusion as described above. A series of horizontal cross-sections of fresh-frozen specimens was performed, and localization of PpIX production was noted by fluorescence microscopy.

Histological examinations were performed to get a qualitative picture of reaction to PDT. A total of 15 specimens were obtained. Eight biopsies of PDT-treated areas were taken with accompanying specimens from the non-treatment area: four from multiple PDT-treated areas at follow-up 5, one from a multiple PDT-treated area at follow-up 3, one from a single PDT-treated area immediately after PDT, one from a single PDT-treated area at follow-up 3, and one from a single PDT-treated area at follow-up 5. Seven biopsies were obtained without an accompanying specimen from control areas, and were analyzed for morphological changes due to PDT: two from single PDT-treated areas immediately after PDT, one from an acneiform lesion appearing at 3 days after PDT, one from a single PDT-treated area at follow-up 2, one from a single PDT-treated area at follow-up 5, and one from a multiple PDT-treated area at follow-up 3.

Statistical Analysis

Treatment effects were determined based on the following analyses: (1) comparing the scores from each follow-up visit to the baseline scores using paired t tests, (2) comparing the change from baseline among the four treatment sites using paired t tests, (3) comparing the change from baseline between the single treatment and multiple treatment groups using two-sample t-tests, and (4) comparing the change from baseline between the single treatment and multiple treatment groups using a repeated measures analysis to combine data from all follow-up visits. Statistical significance was defined as p value of less than 0.05.

Results

Of the 23 subject enrolled, 22 (17 males and 5 females) completed the study. One was dropped from the study because the patient's asthma necessitated systemic steroid treatment, which is one of the exclusion criteria. The age of patients completing the study ranged from 18 to 44 years. Characteristics of the subjects in both groups are shown in Table 1.

TABLE I

Subject characteristics in both groups.

| | Single treatment group | Multiple treatment group |
|---|---|---|
| Age (year) | 30 ± 8.74 | 27 ± 4.56 |
| Gender M/F | 9/2 | 8/3 |
| Skin phototype | Type I 9.1% | Type I 18.2% |
| | Type II 27.3% | Type II 36.4% |
| | Type III 54.5% | Type III 27.3% |
| | Type IV 9.1% | Type IV 18.2% |
| Disease history (year) | 11.45 ± 8.38 | 11.27 ± 4.24 |
| Previous systemic antibiotic treatment (number of subjects) | 3 (27%) | 4 (36%) |
| Previous topical antibiotic treatment (number of subjects) | 3 (27%) | 4 (36%) |
| Previous systemic isotretinoin treatment (number of subjects) | 3 (27%) | 2 (18%) |
| Number of baseline comedo | 4.39 ± 6.68 | 6.48 ± 8.24 |
| Number of baseline inflammatory comedo | 7.68 ± 11.24 | 4.27 ± 5.06 |
| Number of baseline papules | 6.23 ± 5.03 | 7.55 ± 5.67 |
| Number of baseline papules | 0.55 ± 0.90 | 0.43 ± 0.70 |
| Number of baseline Nodules | 0.48 ± 0.90 | 1.32 ± 2.36 |
| Number of baseline cysts | 0.00 ± 0.00 | 0.00 ± 0.00 |

Figure 1B:

An impressive, acute eruption of inflammatory acneiform lesions was observed in the ALA-PDT sites only, in all patients (100%) in both groups, starting approximately 3–4 days post treatment (FIG. 1). The induced lesions were papules, pustules and nodules which lasted for 4 days to 3 weeks in the single treatment group. In the multiple-treatment group, subsequent treatments induced progressively less inflammatory acne, such that almost no new acneiform lesions were observed after treatment 4.

Figure 2A:
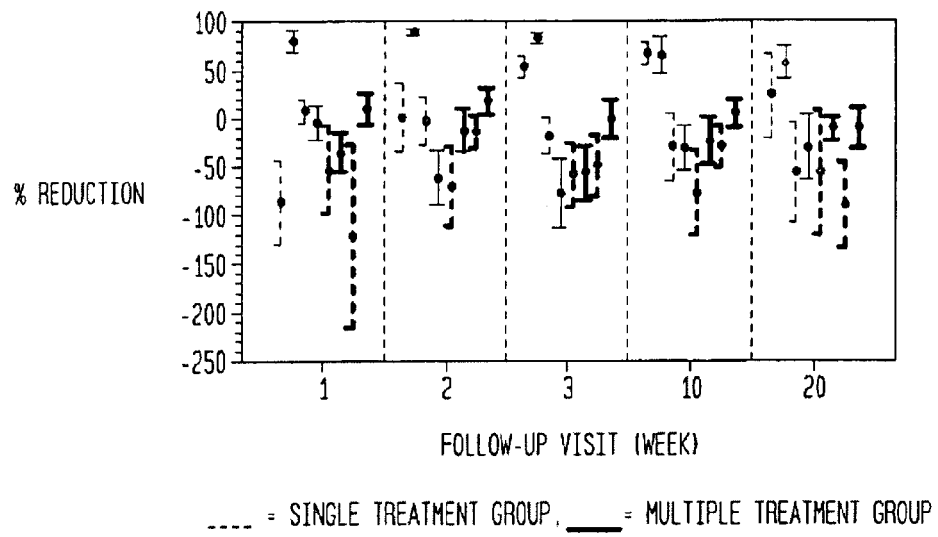
FIG. 2 graphically represents the mean improvement (±SEM) by treatment sites, treatment groups, and follow-up visits, a) Reduction in inflammatory acne score, b) Global clinical-improvement grading, c) Reduction in autofluorescence of follicles, related to P. acnes, and d) Reduction in sebum excretion rate.

Inflammatory Acne Score (FIGS. 2a, 3)

SINGLE TREATMENT GROUP: only the area treated with ALA-PDT showed improvement in acne, which was statistically significant starting 3 weeks after treatment. The other three areas (ALA alone, light alone, untreated) showed slightly worse acne not significantly different than baseline, for all visits. When comparing the change from baseline between the are treated with single ALA-PDT and the other three areas, the differences were statistically significant at 3, 10, 20 weeks.

MULTIPLE TREATMENT GROUP: There was obvious and statistically significant improvement in acne at all follow-up visits after multiple ALA-PDT treatment. There was no improvement in ALA-alone, light along or untreated sites. Change from baseline was significantly greater at sites of multiple ALA-PDT compared with the other three sites for all visits (p<0.05). At visit 2 only (week 2), there was a barely-significant improvement in the area treated with ALA along compared to the untreated area (p=0.046).

COMPARISON BETWEEN SINGLE AND MULTIPLE TREATMENT GROUPS: Multiple ALA-PDT treatments group showed significantly better improvement than the single ALA-PDT treatment group at the first 3 follow-up visits. This difference diminished after week 3. No significant differences between multiple and single treatment group were observed in the non-PDT sites with respect to each individual visit. When data from all follow-up visits were combined, the multiple ALA-PDT and multiple ALA alone treatment sites had better improvement than the single treatment group (p<0.001 and P=0.007, respectively).

Figure 2B:
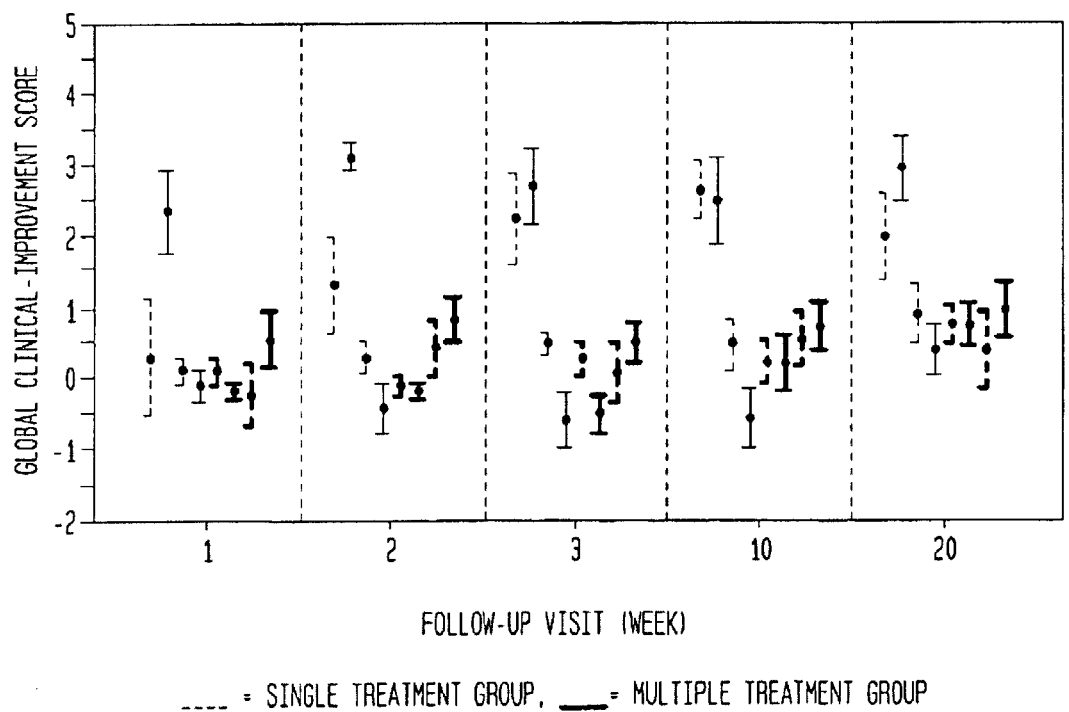
Figure 3A:
FIG. 3 demonstrates inflammatory acne improved by a single PDT treatment, a) Baseline, b) 10 weeks post PDT, c) Acne starts to resume 20 weeks after PDT, Long-term remission of acne after multiple PDT treatments. d) Baseline, e) 2 weeks post PDT (an irritation reaction to Sebutape is seen on the right side in this subject), f) 20 weeks post PDT.
Figure 3B:
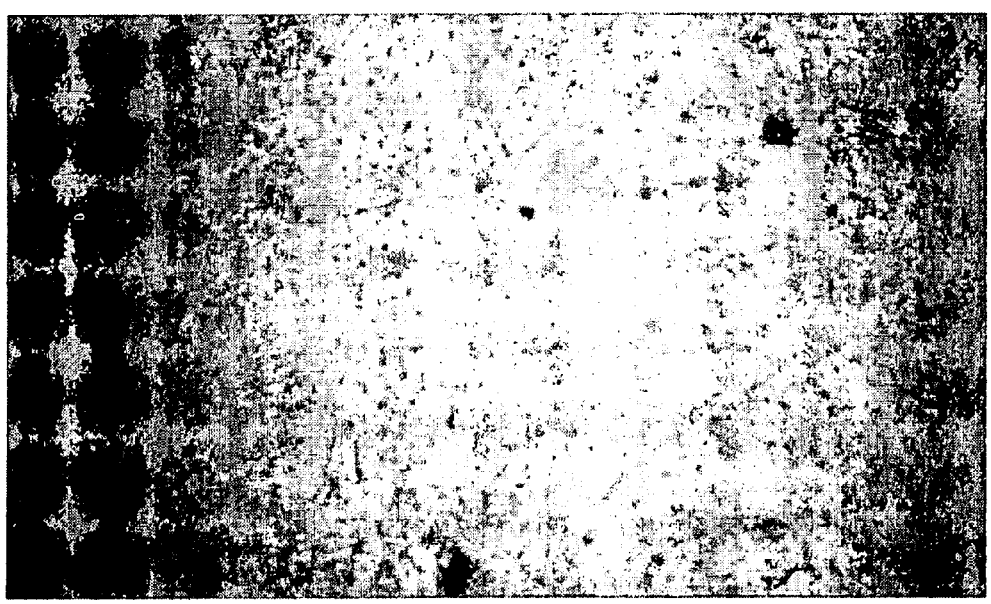
Figure 3C:
Figure 3D:
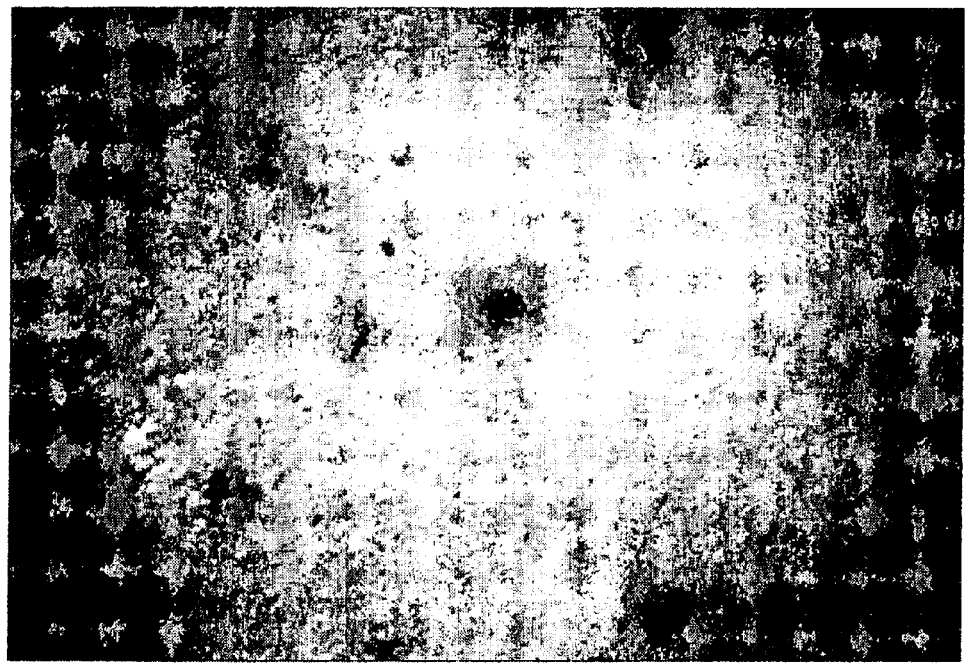
Figure 3E:
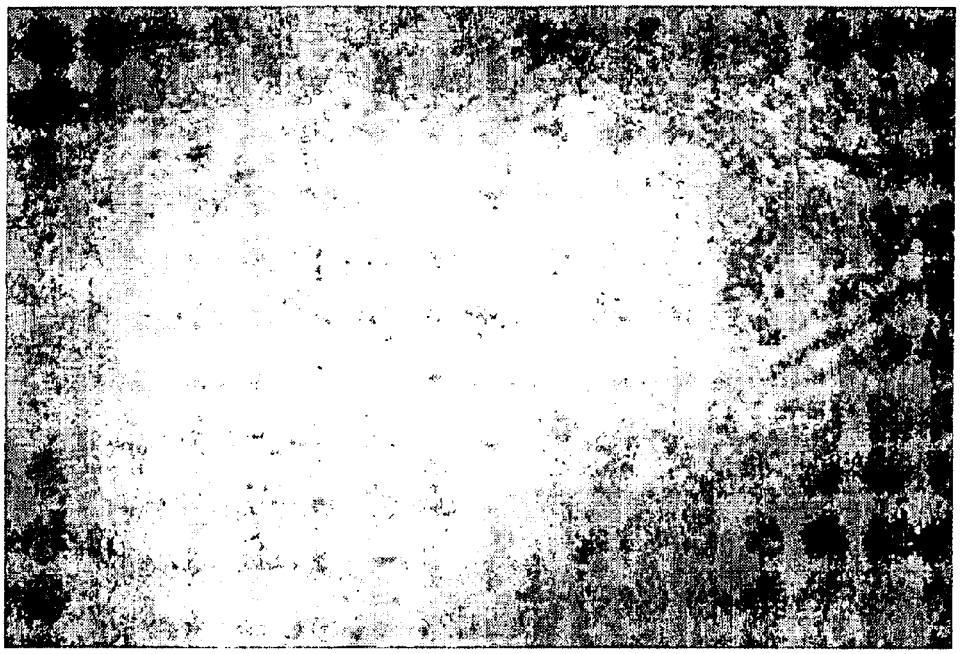
Figure 3F:
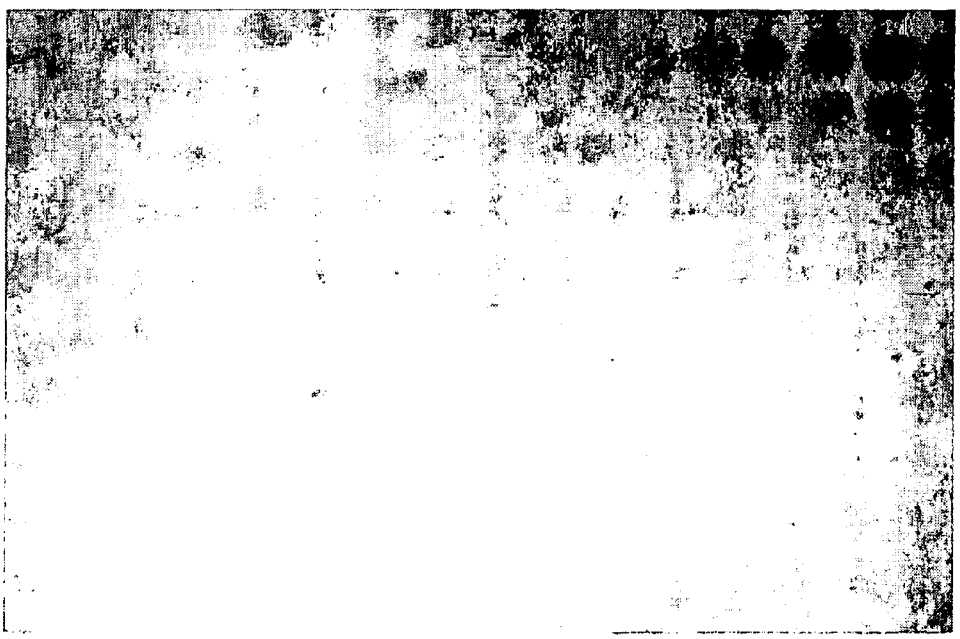

Global Clinical-improvement Score (FIG. 2b)

SINGLE TREATMENT GROUP: The ALA-PDT site showed significant global improvement starting week 3 and extending through week 20, The area without treatment, and the area treated with light alone, also showed improvement reaching statistical significant at weeks 3 and 20 (p=0.017 and 0.018), respectively. The difference between ALA-PDT and the other three treatment sites was statistically significant at weeks 3 and 10.

MULTIPLE TREATMENT GROUP: Significant improvement for the ALA-PDT related area was observed starting visit 1 (week 1) and this improvement persisted throughout all of the 4 follow-up visits (up to 20 weeks at least). The area treated with ALA alone at visit 2 and the area treated with light alone or ALA alone at visit 5 also showed improvement reaching statistical significance. However, there was a significantly better improvement in the ALA-PDT treated site than the other 3 sites, at all follow-up visits.

COMPARISON BETWEEN SINGLE AND MULTIPLE TREATMENT GROUPS: The multiple ALA-PDT treatments group had significantly better improvement than the single ALA-PDT treatment group when evaluated at the first 2 follow-up visits (week 1 & 2). The single-treatment group did not have significant better acne improvement than multiple treatment, at any time. When data from all follow-up visits were combined, the comparison between single ALA-PDT and multiple ALA-PDT reached statistical significance (p=0.008).

Figure 4:
FIG. 4 shows the fluorescence of porphyrin from bacteria in follicles (red dots) decrease after a single ALA-PDT, Photography was taken as described at baseline (a), week 2 (b), week 10 (c), and week 20 (d) post-PDT.
Figure 4:
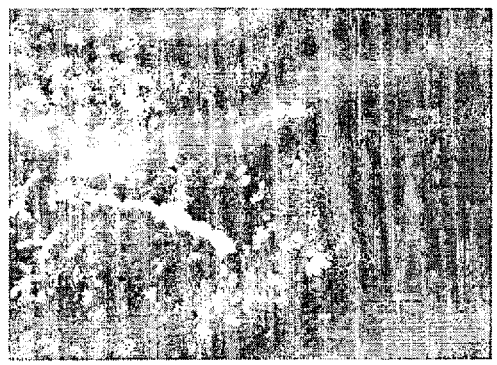
Figure 4:
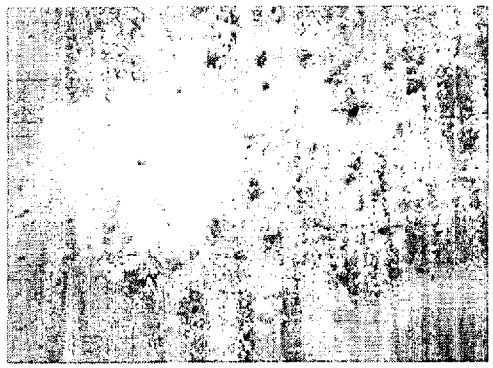
Figure 4:
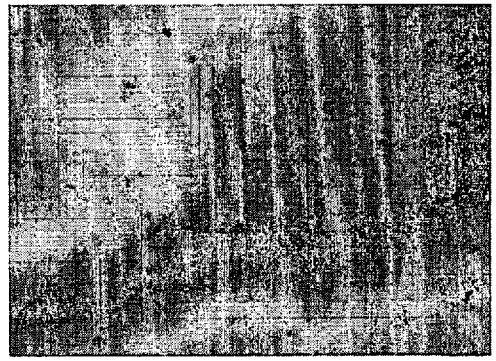

Fluorescence Photography Evaluation (FIGS. 2c, 4)

SINGLE TREATMENT GROUP: Only the ALA-PDT-treated sites showed significant loss of fluorescence related to P. acnes, which lasted for all 4 follow-up visits. The differences between ALA-PDT and the other 3 test sites were also statistically significant for all visits.

MULTIPLE TREATMENT GROUP: Again, only the ALA-PDT sites showed significant loss of P. acnes, fluorescence, starting at follow-up visit 2. The sites treated with ALA alone or untreated had significantly greater fluorescence than baseline, at week 10 and 20. The differences between the ALA-PDT area and the other 3 test sites was statistically significant for all visits.

COMPARISON BETWEEN SINGLE AND MULTIPLE TREATMENT GROUPS: The group treated four times with ALA-PDT had better, but not significant, improvement than those treated with single ALA-PDT. Combining data from all visits, the difference in fluorescence related to P. acnes between single and multiple treatment groups still did not reach statistical significance (p=0.081).

Figure 5:
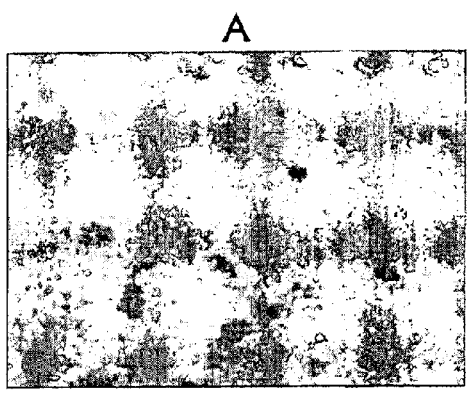
FIG. 5 demonstrates that sebum excretion is suppressed by a single ALA-PDT application, then gradually recovers, at baseline (a), week 2 (b), week 10 (c), week 20 (d) post-PDT.
Figure 5:
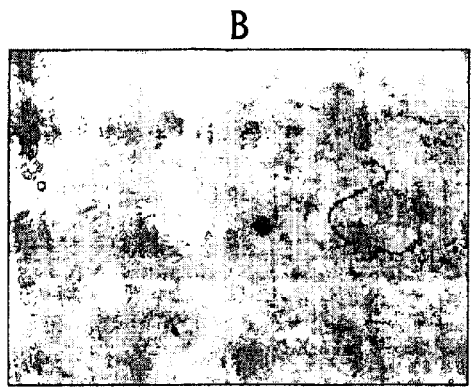
Figure 5:
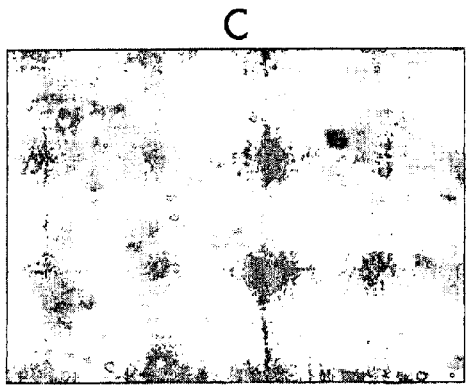
Figure 5:
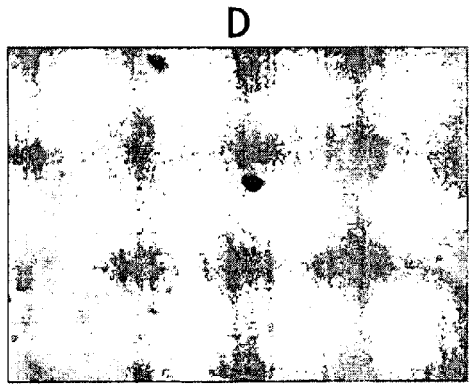
Figure 6:
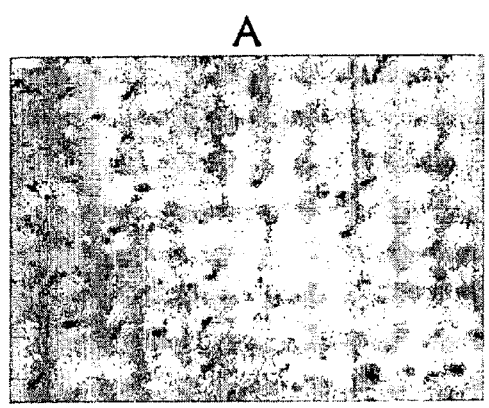
FIG. 6 demonstrates that Sebum excretion remains suppressed after multiple ALA-PDT treatments, for at least 20 weeks, (a) (b) (c) (d) as in FIG. 8.
Figure 6:
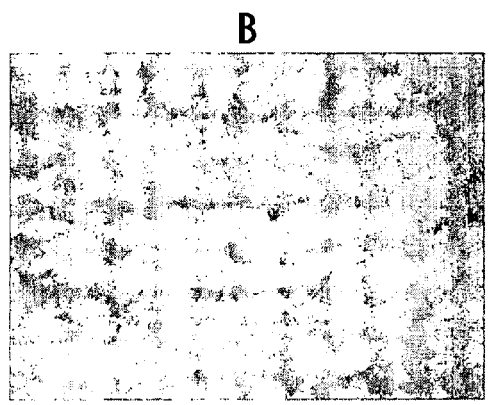
Figure 6:
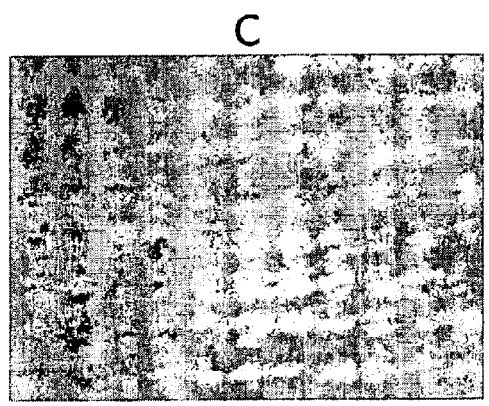
Figure 6:
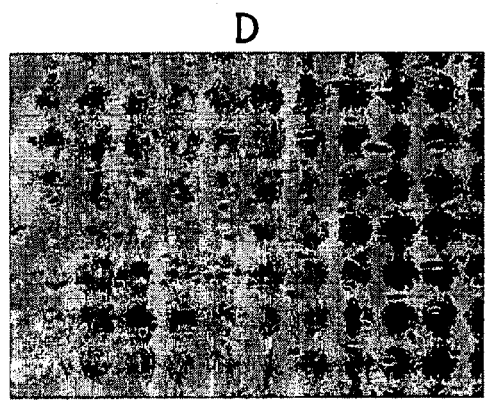

Sebum Excretion Rate (SER) (FIGS. 2d, 5, 6)

SINGLE TREATMENT GROUP: Only the area treated with ALA-PDT showed a significant decrease of SER, which was at weeks 2, 3, 20. The SER in the area treated with PDT was also significantly lower than any other test sites, at each follow-up visit.

MULTIPLE TREATMENT GROUP: The ALA-PDT sites showed significant decrease in SER, at all follow-up visits. The differences between the area treated with ALA-PDT and the other 3 areas were also statistically significant at all 4 visits.

COMPARISON BETWEEN SINGLE AND MULTIPLE TREATMENT

GROUPS: Multiple ALA-PDT suppressed SER more than single ALA-PDT; however, the difference was significant only at the longest follow-up time, 20 weeks. When data from all follow-up visits were combined, multiple ALA-PDT caused far lower SER than single ALA-PDT (p=0.001).

History

Figure 7A:
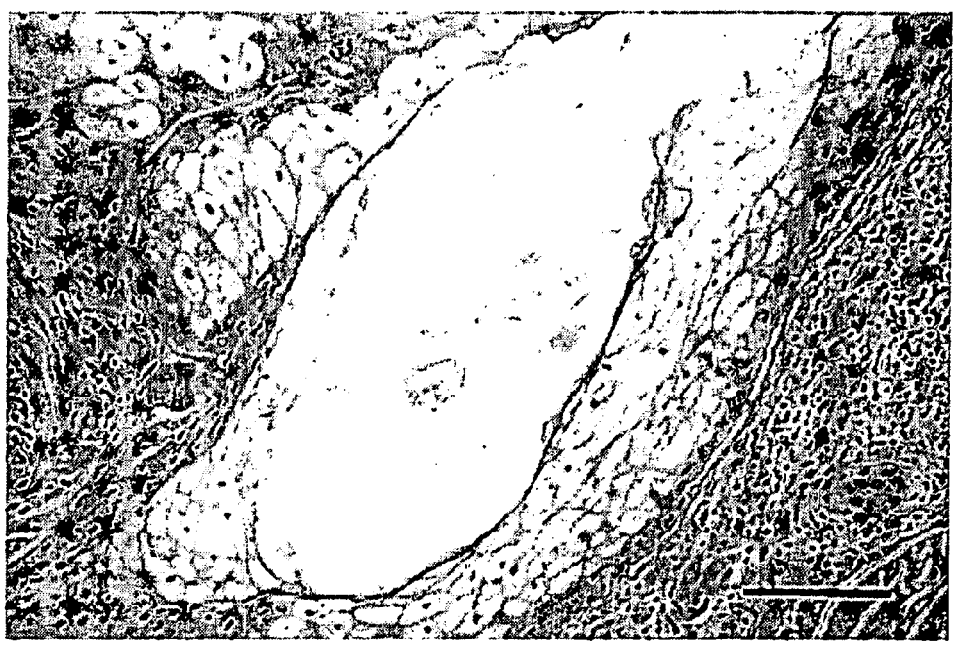
FIG. 7 depicts retiform degeneration of sebocytes (a) and intense mixed neutrophil-predominant infiltrate (b), the biopsies were taken immediately after a single ALA-PDT treatment. Scale bars, 100 $\mu$m.
Figure 7B:
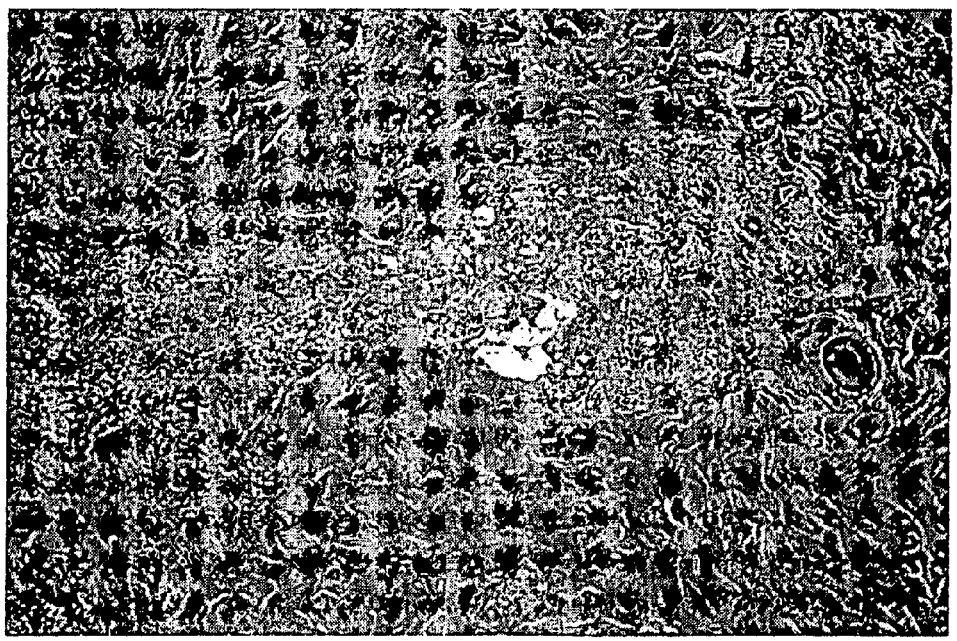
Figure 8A:
FIG. 8 shows that neutrophillic pustules are seen 3 days after ALA-PDT, intraepidermally, (a) and within pilosebaceous units (b), associated with the acneiform eruption caused by ALA-PDT. The sections were stained with hemotoxylin & eosin (a & b), Scale bars, 100 $\mu$m.
Figure 8B:
Figure 9:
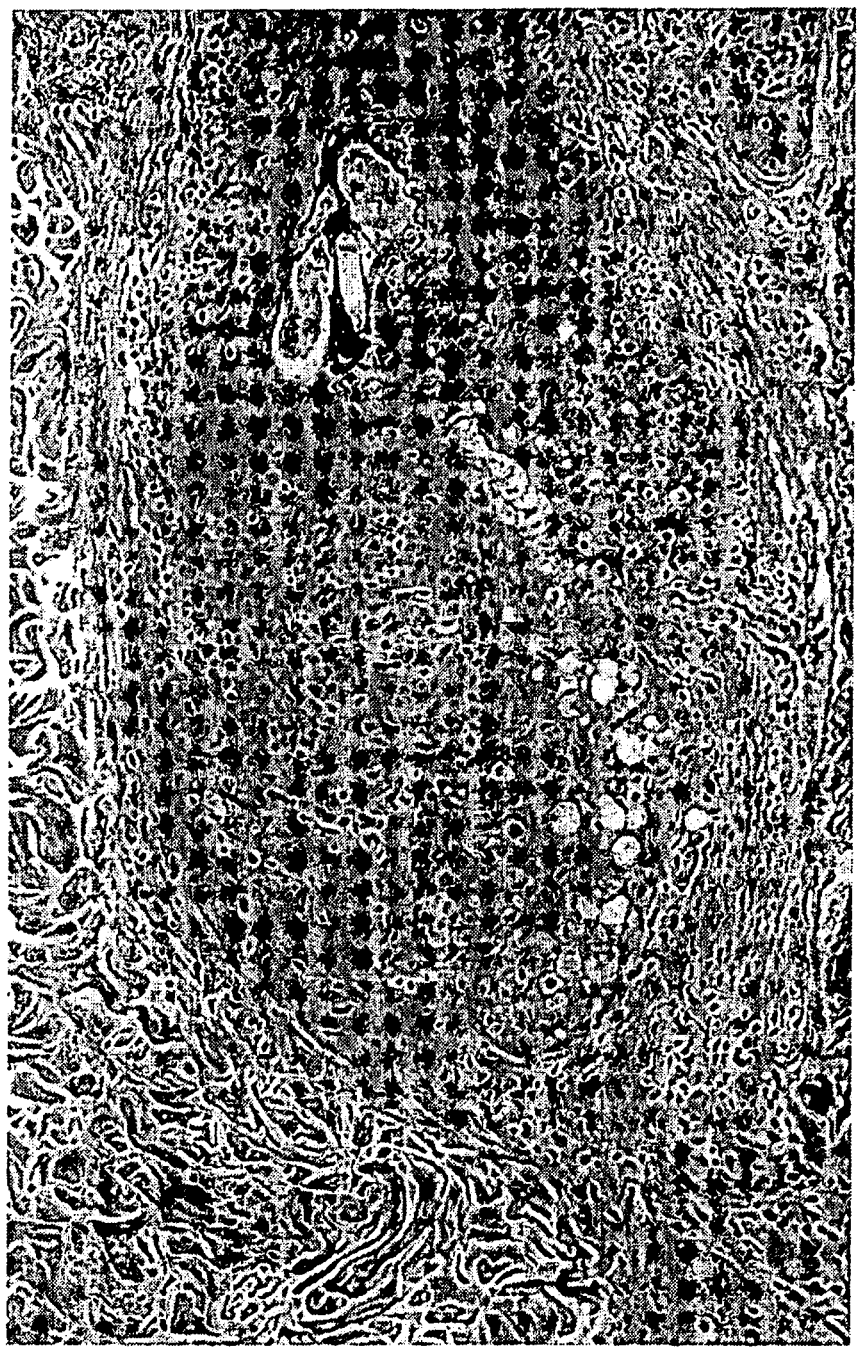
FIG. 9 depicts focal vacuolization of sebocytes and follicular keratinocytes, this biopsy was taken at week 3 from single ALA-PDT-treated skin, note the mild perifollicular fibrosis, Scale bar, 100 $\mu$m.
Figure 10A:
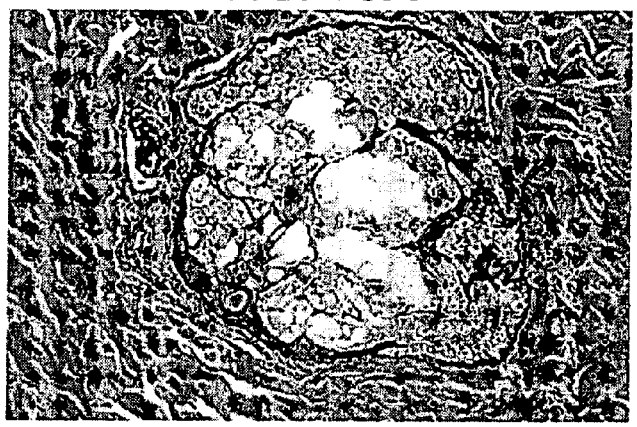
FIG. 10 is a graphical representation of long-term damaged pilosebaceous unit caused by ALA-PDT, twenty weeks after 4 ALA-PDT treatments, there are atrophic or partially damaged sebaceous glands (a), a granulomatous reaction in completely destroyed sebaceous glands (b), obliterated hair follicles (c), and perifollicular fibrosis (c). Scale bars, 100 $\mu$m.
Figure 10B:
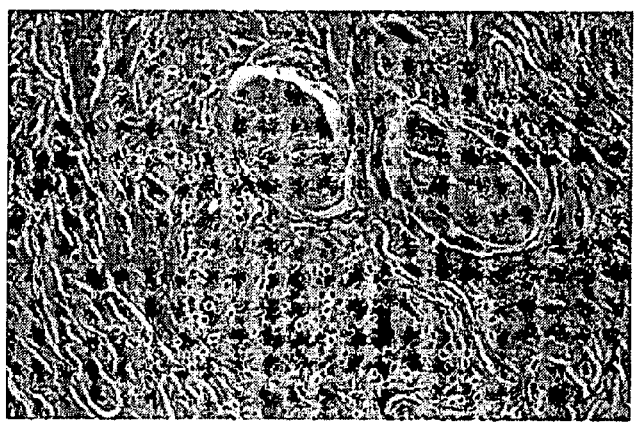
Figure 10C:
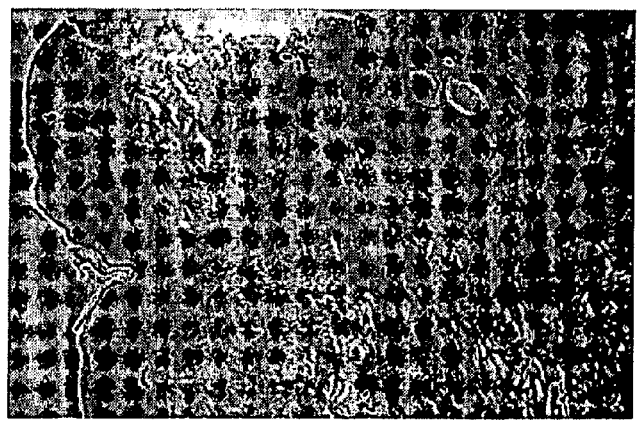

Marked focal histologic changes in pilosebaceous glands were observed in all samples treated by ALA-PDT. In the control (untreated) biopsy specimens, all subjects had well-developed sebaceous gland with typical round or oval locules. Immediately after ALA-PDT, there was a mixed, neutrophil-predominant infiltrate along pilosebaceous units and perivascular area, and retiform degeneration of sebocytes (FIG. 7). There was an apparent reduction of sebaceous gland size, with a mean decrease of 40% immediate after PDT. Epidermal changes were also observed with epidermal necrosis, vacuolizaiton of keratinocytes from the mid stratum spinulosum to the stratum granulosum, and neutrophilic exocytosis. At 3 days after PDT, the acneiform lesions induced by PDT showed large intraepiderman pustules, disruption of hair follicles, and frank sebaceous gland destruction replaced by a mixed, neutrophil-predominant dermal infiltrate (FIG. 8). Reduction of sebaceous gland size compared with untreated control area was observed 3 weeks after both single and multiple ALA-PDT (30% vs. 55%). Focal vacuolization of sebocytes (FIG. 9), granulomatous reaction, and perifollicular fibrosis were also observed, although some of the sebaceous glands had regained a normal morphology with smaller size relative to control. Cytoplasm/nuclear cross-section area ratio in sebocyte was reduced, relative to non-treatment, by 38% and 56% in single and multiple PDT, respectively. In the multiple treatment group, improvement contained longer into the follow-up period, such that by the end of the study (20 weeks after the last treatment), reduction of sebaceous gland size and sebocyte cytoplasm/nuclear area were 45% (range from 15–80%) and 46% (range from 39–80%) and 46% (range from 39–53%) respectively. At 20 weeks after multiple ALA-PDT treatments, there was complete destruction or 25 marked atrophy of sebaceous gland lobules, with comparatively few sebocytes present (FIG. 10a). Frequently, a granulomatous reaction composed of multinucleated giant cells and histiocytic infiltrates was seen at the remnant of destroyed sebaceous glands (FIG. 10b). Perifollicular fibrosis (FIG. 10c), inflammation and spongiosis were seen occasionally, but these findings were not constant. The epidermis appeared completely normal.

Twenty weeks after a single ALA-PDT treatment, there was only a slight reduction of sebaceous gland size (a mean decrease of 17%) without other apparent morphological changes or infiltrates. The sebocyte cytoplasm/nuclear area ratio was not reduced. Masson-trichrome stained specimens showed perifollicular fibrosis caused by single or multiple ALA-PDT, and mild disarray of collagen bundles in the mid-reticular dermis by multiple ALA-PDT. Fontana-Masson stain showed higher epidermal pigmentation after ALA-PDT, and slightly more dermal melanophages (pigment incontinence) compared with untreated sites.

Figure 11:
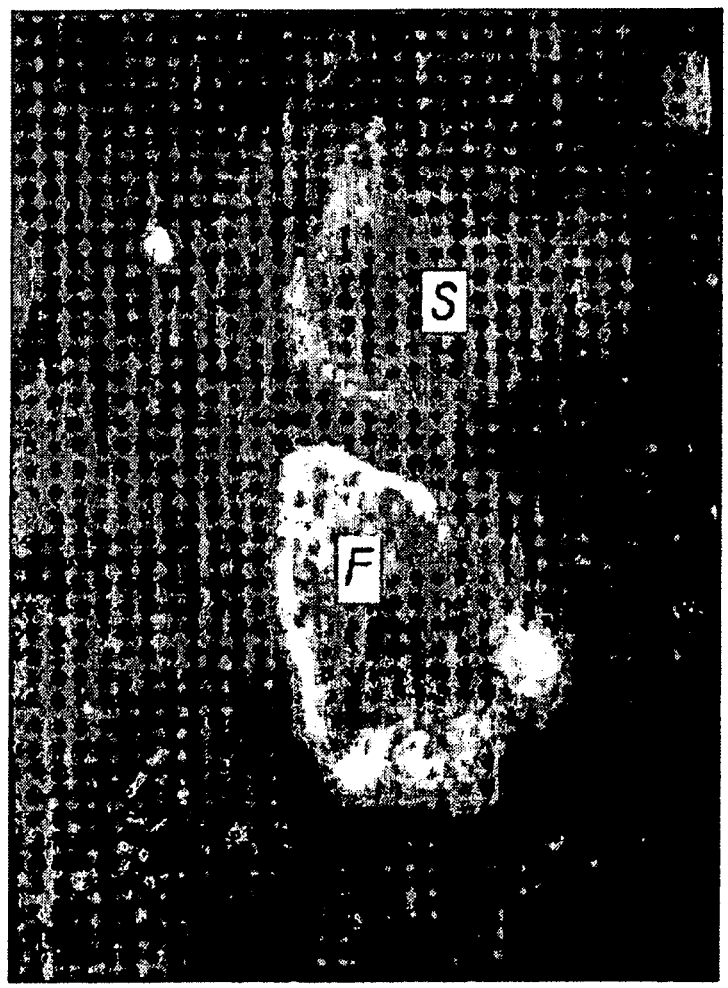
FIG. 11 are Fluorescence Micrographs, a) Fluorescence microscopy demonstrates PpIX production is mainly located in sebaceous glands (S) and hair follicles (F), Fluorescence is greater in sebaceous glands, compared to that in hair follicles.

Fluorescence microscopy of fresh-frozen sections after ALA application, showed bright porphyrin fluorescence in epidermis and pilosebaceous units, compared with untreated skin. There was brighter PpIX fluorescence in sebocytes than in the adjacent follicular epithelial cells (FIG. 11).

Adverse Effects

Erythema and edema were most intense about 10 minutes after the beginning of PDT and subsided to lesser intensity by the end of the light exposure. There was a substantial decrease in erythema and edema by 1 hour after treatment, in both groups. Subjective reports of pain, burning, and itch were more severe at 10 minutes after starting PDT than at the end of treatment. A burning sensation became more severe with subsequent treatments and was the main complaint (9, 67%, 67%, and 73% of subjects at treatment 1, 2, 3, and 4 respectively). Itching was the next frequent subjective side effect of subsequent treatments (73, 73, 55, and 55% of subjects at treatment 1, 2, 3 and 4). In contrast to multiple ALA-PDT, itching was the main discomfort in the single ALA-PDT group, and pain was the least.

Erythema, hyperpigmentation, and exfoliation were commonly seen after PDT. Six patients in the multiple treatment group could not continue the weekly treatment scheme and had to postpone their next treatment: two at treatment 3 and 4, two at treatment 3, and 2 at treatment 4. Erythema and hyperpigmentation faded away completely at 20 weeks in 82% and 91% of the single-treatment subjects, respectively. None of the subjects had exfoliation after 3 weeks post treatment. One subject in the single ALA-PDT group developed blistering in the PDT site, after vigorous aerobic exercise while wearing a tight outfit the day after treatment. This area healed without scarring in 3 weeks. In fact, no site in any subject had any scarring. Multiple PDT caused long-lasting hyperpigmentation with 55% of subjects still showing some degree of pigmentation at 20 weeks after treatment. In 10% of multiple-treatment subjects, superficial but very prominent exfoliation was seen after 4 treatments, with transient purpura (average 1 week) and partial loss of epidermis.

Discussion

Figure 12:
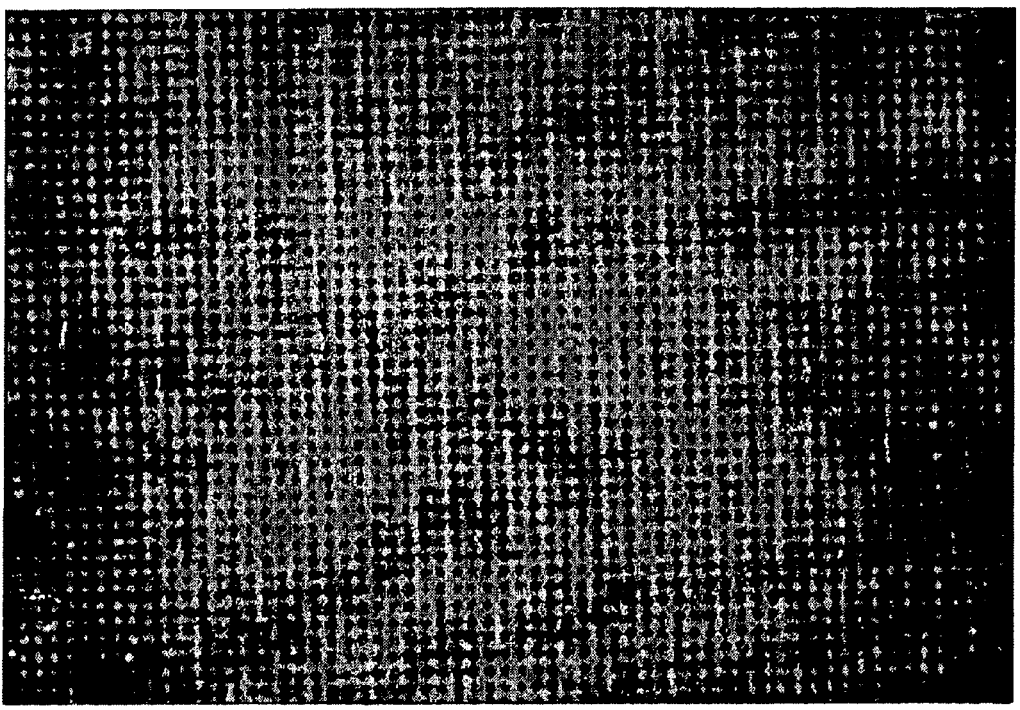
FIG. 12 demonstrates that ALA-induced PpIX fluorescence is greater in acne lesions than surrounding tissue.

The present invention demonstrates by fluorescence photography that ALA-induced PpIX fluorescence is greater in acne lesions than surrounding tissue (FIG. 12). *P. acnes* bacteria produce porphyrins to the extent that red fluorescence is easily seen, and is correlated with *P. acnes* colonization of sebaceous follicles. Topical ALA-PDT can, therefore, have several modes of action for acne treatment. Direct photodynamic injury of sebaceous glands can inhibit sebum production; photodynamic killing of *P. acnes* can sterilize sebaceous follicles; follicular obstruction can be reduced by changing keratinocyte shedding and hyperkeratosis. The present invention provides that topical ALA-PDT has potent effects on acne vulgaris. Blinded clinical assessment showed obvious and significant improvement of acne for at least 10 weeks after a single ALA-PDT treatment, and for at least 20 weeks after 4 treatments. Surprisingly, even nodular acne responded well and cystic acne induced by ALA-PDT resolved quickly and completely. ALA-PDT caused acute inflammation followed by partial or complete necrosis of sebaceous glands, producing a monomorphic acneiform eruption which appeared after a few days and then subsided over several days to weeks. A similar eruption often occurs after starting systemic retinoids, which like ALA-PDT, strongly inhibit sebaceous gland activity. Sebum excretion was inhibited abruptly by ALA-PDT, then slowly and only partially recovered by 20 weeks after 4 ALA-PDT treatments. Histologically, sebaceous glands were smaller, and remained so long after ALA-PDT. Fluorescence of the endogenous porphyrins associated with *P. acnes* was also significantly decreased after both single and multiple ALA-PDT, for at least 20 weeks. Not to be limited by theory, it is believed that antibiotic effects on *P. acnes* can be readily achieved by a single ALA-PDT treatment. Taken together, the present invention provides that topical ALA-PDT inhibits multiple pathogenetic factors of acne.

The acneiform eruption which appears 34 days after the first ALA-PDT treatment was a constant finding in this study. The mechanism for this eruption is unknown. It is believed that ALA-PDT disrupts sebocyte and *P. acnes* membranes, activating complement and neutrophil migration into the perifollicular area. Reactive oxygen species produced by neutrophils play a significant role in disrupting the follicular epithelium, which is responsible for the inflammatory process of acne. In addition, *P. acnes* activates complement and produces C5a, a potent neutrophil chemotactic factor. The bacterial cell wall peptidoglycan-polysaccharide substance may also lay a role in stimulating an immune granuloma type reaction, which was seen in this study following multiple ALA-PDT. In the multiple-treatment group, each subsequent ALA-PDT treatment produced a progressively less inflammatory and weaker acneiform eruption, which is at least consistent with sterilization of the follicles by the first treatment.

ALA-PDT is a simple procedure, and has very little side-effects. Fortunately, there was no scarring in this study, after a total of about 60 PDT sessions in 23 subjects. However, each treatment takes time, can sometimes be painful or pruritic, can cause erythema and edema, occasionally causes blistering and purpura, causes an acute acneiform eruption, and usually leads to hyperpigmentation which fades gradually over weeks to months. To most people, these side-effects would be tolerable in practice when ALA-PDT were to provide a permanent improvement in acne. This situation is not unlike the use of systemic retinoids, which produce both long-lasting benefits and major side-effects.

Equivalents

Those of ordinary skill in the art will recognize, or be able to ascertain, using no more than routine experimentation, many equivalents to specific embodiments of the invention described specifically herein. Such equivalents are intended to be encompassed in the scope of the following claims.

What is claimed is:

1. A method for treating at least one of acne vulgaris, acne rosacea, and sebaceous gland hyperplasia comprising the steps of:

a) topically applying 5-aminolevulinic acid (ALA) at a low dose in a range between about 0.10 and 1.0 percent by weight to a section of skin afflicted with at least one of acne vulgaris, acne rosacea, and sebaceous gland hyperplasia, wherein the ALA is compounded for delivery, to sebaceous glands and is converted into a photosensitizing agent actuable by energy that penetrates outer layers of epidermis; and b) exposing the infiltrated section of skin to energy to cause the photosensitizing agent to become photodynamically activated to kill bacteria and thereby treat at least one of acne vulgaris, acne rosacea, and sebaceous gland hyperplasia without modifying the sebaceous gland.

2. The method of claim 1, further including the step of waiting for the ALA to be metabolized to PpIX before exposing the infiltrated section of skin.

3. The method of claim 1, wherein the infiltrated section of skin is exposed to energy in the range of about 1 to 20 J/cm$^2$.

4. The method of claim 3, wherein an energy source for the energy is selected from among i) a laser, such as a pulsed dye laser or laser diode array, and ii) sunlight.

5. The method of claim 1, wherein the energy has a wavelength in the range of between about 320 and about 700 nm.

6. The method of claim 1, wherein the energy has a wavelength in the range of between about 550 and about 600 nm.

7. The method of claim 1, wherein the ALA is suspended in a pharmaceutical carrier.

8. The method of claim 7, wherein said pharmaceutical carrier is selected from among a liposome and an aqueous solution.

9. The method of claim 1, wherein the ALA is compounded to penetrate the skin via a pilosebaceous unit.

10. The method of claim 1, further comprising the step of applying ultrasound to drive the ALA into spaces in the skin.

11. The method of claim 1, wherein the ALA is compounded to enter spaces in hair ducts in the skin not occupied by hair.

12. The method of claim 1, wherein the ALA is compounded to enter space within sebaceous glands.

13. A method for the treatment or prevention of at least one of acne vulgaris, acne rosacea, and sebaceous gland hyperplasia, comprising the steps of:

a) topically applying 5-amino levulinic acid (ALA) to skin and a substance which absorbs UV radiation in the UVA or UVB range, wherein the ALA is converted into a photosensitizing agent that is activated by energy which penetrates outer layers of epidermis;

b) causing a sufficient amount of ALA to infiltrate the pilosebaceous unit; and c) exposing the infiltrated section of skin to sunlight in the range of about 1 to about 50 J/cm$^2$ to cause the photosensitizing agent to become photodynamically activated eradicating the bacteria associated with at least one of acne vulgaris, acne rosacea, and sebaceous gland hyperplasia.

* * * * *